US011625951B2

(12) United States Patent
Wittnebel et al.

(10) Patent No.: US 11,625,951 B2
(45) Date of Patent: Apr. 11, 2023

(54) SYSTEM AND METHOD OF UTILIZING COMPUTER-AIDED IDENTIFICATION WITH MEDICAL PROCEDURES

(71) Applicant: ALCON INC., Fribourg (CH)

(72) Inventors: Michael Wittnebel, Hirschaid (DE); Oliver Kern, Herzogenaurach (DE)

(73) Assignee: Alcon Inc., Fribourg (CH)

( * ) Notice: Subject to any disclaimer, the term of this patent is extended or adjusted under 35 U.S.C. 154(b) by 313 days.

(21) Appl. No.: 17/008,301

(22) Filed: Aug. 31, 2020

(65) Prior Publication Data

US 2021/0081667 A1 Mar. 18, 2021

Related U.S. Application Data

(60) Provisional application No. 62/899,988, filed on Sep. 13, 2019.

(51) Int. Cl.
*G06V 40/18* (2022.01)
*A61B 3/12* (2006.01)

(52) U.S. Cl.
CPC .......... *G06V 40/197* (2022.01); *A61B 3/1216* (2013.01)

(58) Field of Classification Search
CPC ............................ G06V 40/197; A61B 3/1216
See application file for complete search history.

(56) References Cited

U.S. PATENT DOCUMENTS

| 5,291,560 A | 3/1994 | Daugman |
| 2006/0165266 A1 | 7/2006 | Hamza |
| 2009/0115892 A1 | 5/2009 | Sako |
| 2019/0027247 A1 | 1/2019 | Soto Santos |

FOREIGN PATENT DOCUMENTS

| EP | 1924084 A2 | 5/2008 |
| WO | 2012135073 A2 | 10/2012 |
| WO | WO 2012135073 A2 * | 10/2012 |

OTHER PUBLICATIONS

Filatova, et al. "Biometrische Identifikationsverfahren" [Biometric identification methods]. 2004. Humboldt Universitat zu Berlin—Institut fur Informatik [Department of Computer Science, Humboldt University of Berlin] Retrieved from the Internet on Jan. 6, 2021. https://www2.informatik.hu-berlin.de/Forschung_Lehre/algorithmenII/Lehre/SS2004/Biometrie/03Iris/iris.pdf.

\* cited by examiner

*Primary Examiner* — Edward Park

(57) ABSTRACT

The disclosure provides a system that may receive an identification of a first patient; may retrieve, based at least on the identification of the first patient, first eye identification information that includes a first plurality of iris structures associated with a first eye of the first patient; may determine a second plurality of iris structures of an eye of a current patient; may determine if the second plurality of iris structures match the first plurality of iris structures; if the second plurality of iris structures match the first plurality of iris structures, may provide an indication that the first eye has been correctly identified; and if the second plurality of iris structures do match the first plurality of iris structures, may provide an indication that the first eye has not been correctly identified.

14 Claims, 21 Drawing Sheets

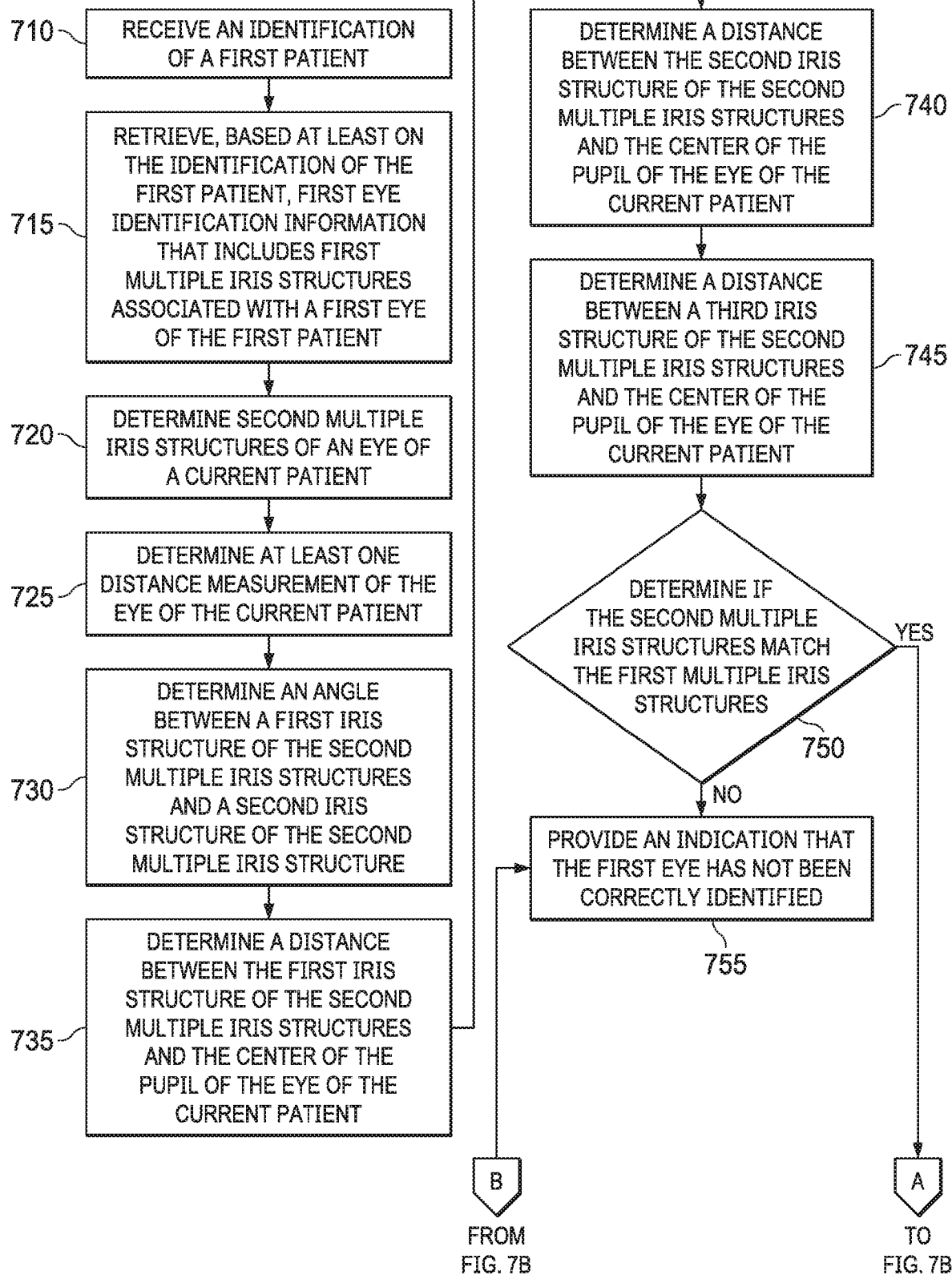

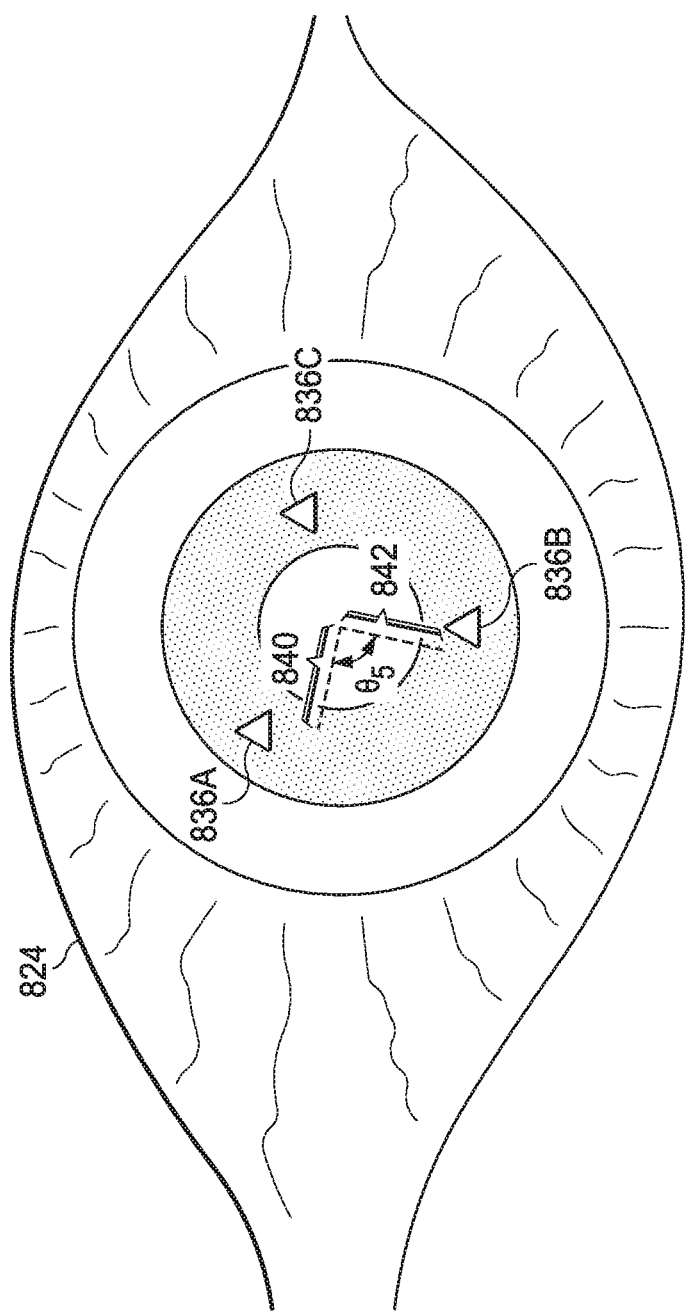

SYSTEM AND METHOD OF UTILIZING COMPUTER-AIDED IDENTIFICATION WITH MEDICAL PROCEDURES

BACKGROUND

Field of the Disclosure

This disclosure relates to computer-aided identification and more particularly to utilizing computer-aided identification with medical procedures.

Description of the Related Art

In the past, a failure to correctly identify a patient could result in transfusion errors, medication errors, incorrect person procedures, testing errors, and/or wrong medical procedure site errors, among others. Patient misidentification can be a root cause in medical procedure errors. Areas where patient misidentification can occur include surgical interventions, blood transfusions, drug administration, and/or phlebotomy, among others. Patient misidentification can be caused by name structures (e.g., close similarity of names), inaccuracies dates of births, clothing that conceals identity, non-conscious patients, errors when registering patients via computerized systems, an identification wrist band not present, an identification wrist band that identifies another (e.g., incorrect) patient, etc. Furthermore, a failure to correctly identify an eye of a patient could also result in transfusion errors, medication errors, incorrect person procedures, testing errors, and/or wrong medical procedure site errors, among others.

SUMMARY

The present disclosure provides a system able to receive an identification of a first patient. In one example, the system may receive the identification of the first patient from medical personnel. In another example, the system may receive the identification of the first patient via scanning a wristband of the patient. The system may further retrieve, based at least on the identification of the first patient, first eye identification information that includes first multiple iris structures associated with a first eye of the first patient. The system may further determine second multiple iris structures of an eye of a current patient. The system may further determine if the second multiple iris structures match the first multiple iris structures. If the second multiple iris structures match the first multiple iris structures, the system may further provide an indication that the first eye has been correctly identified. If the second multiple iris structures do not match the first multiple iris structures, the system may further provide an indication that the first eye has not been correctly identified.

The first eye identification information may further include at least one distance measurement associated with the first eye. For example, the at least one distance measurement associated with the first eye may include at least one of a distance measurement from a cornea of the first eye to a lens of the first eye, a distance measurement from a lens of the first eye to a retina of the first eye, a corneal thickness of the first eye, and a lens thickness of the first eye. The system may further determine at least one distance measurement of the eye of the current patient. For example, the at least one distance measurement associated with the eye of the current patient may include at least one of a distance measurement from a cornea of the eye of the current patient to a lens of the eye of the current patient, a distance measurement from a lens of the eye of the current patient to a retina of the eye of the current patient, a corneal thickness of the eye of the current patient, and a lens thickness of the eye of the current patient. The system may further determine if the at least one distance measurement of the eye of the current patient matches the at least one distance measurement associated with the first eye. If the second multiple iris structures match the first multiple iris structures and the at least one distance measurement of the eye of the current patient matches the at least one distance measurement associated with the first eye, the system may perform providing the indication that the first eye has been correctly identified. If the at least one distance measurement of the eye of the current patient does not match the at least one distance measurement associated with the first eye, the system may perform providing the indication that the first eye has not been correctly identified.

The system may further retrieve medical procedure information based at least on one of the identification of the first patient and the second multiple iris structures of the eye of the current patient. The system may further provide, via at least one of a display and a microscope integrated display, the medical procedure information.

A first iris structure of the first multiple iris structures may be separated from a second iris structure of the first multiple iris structures by an first angle with respect to a center of a pupil of the first eye. A first iris structure of the second multiple iris structures may be separated from a second iris structure of the second multiple iris structures by a second angle with respect to a center of a pupil of the eye of the current patient. For example, to determine if the second multiple iris structures match the first multiple iris structures, the system may further determine if second angle matches the first angle.

The first iris structure of the first multiple iris structures may be at a first distance from the center of the pupil of the first eye. The first iris structure of the second multiple iris structures may be at a second distance from the center of the pupil of the eye of the current patient. For example, to determine if the second multiple iris structures match the first multiple iris structures, the system may further determine if the second distance matches the first distance.

The current patient may be the first patient. The eye of the current patient may be a second eye of the first patient, different from the first eye. In one example, the first eye may be a right eye of the patient, and the second eye may be a left eye of the patient. In another example, the first eye may be a left eye of the patient, and the second eye may be a right eye of the patient.

The present disclosure further includes a non-transient computer-readable memory device with instructions that, when executed by a processor of a system, cause the system to perform the above steps. The present disclosure further includes a system or a non-transient computer-readable memory device as described above with one or more of the following features, which may be used in combination with one another unless clearly mutually exclusive: i) receive an identification of a first patient; ii) retrieve, based at least on the identification of the first patient, first eye identification information that includes first multiple iris structures associated with a first eye of the first patient; iii) determine second multiple iris structures of an eye of a current patient; iv) determine if the second multiple iris structures match the first multiple iris structures; v) if the second multiple iris structures match the first multiple iris structures, provide an indication that the first eye has been correctly identified; vi)

if the second multiple iris structures do not match the first multiple iris structures, provide an indication that the first eye has not been correctly identified; vii) determine at least one distance measurement of the eye of the current patient; vi) determine if the at least one distance measurement of the eye of the current patient matches the at least one distance measurement associated with the first eye; viii) if the second multiple iris structures match the first multiple iris structures and the at least one distance measurement of the eye of the current patient matches the at least one distance measurement associated with the first eye, perform providing the indication that the first eye has been correctly identified; ix) if the at least one distance measurement of the eye of the current patient does not match the at least one distance measurement associated with the first eye, perform providing the indication that the first eye has not been correctly identified; x) retrieve medical procedure information based at least on one of the identification of the first patient and the second multiple iris structures of the eye of the current patient; and xi) provide, via at least one of a display and a microscope integrated display, the medical procedure information;

Any of the above systems may be able to perform any of the above methods and any of the above non-transient computer-readable memory devices may be able to cause a system to perform any of the above methods. Any of the above methods may be implemented on any of the above systems or using any of the above non-transient computer-readable memory devices.

It is to be understood that both the foregoing general description and the following detailed description are examples and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

For a more complete understanding of the present disclosure and its features and advantages, reference is now made to the following description, taken in conjunction with the accompanying drawings, which are not drawn to scale, and in which:

FIGS. 7A and 7B illustrate an example of a method of operating a medical system;

FIGS. 8E and 8F illustrate examples of measurements of structures of an iris of another eye of a current patient;

DETAILED DESCRIPTION

Figure 1A:
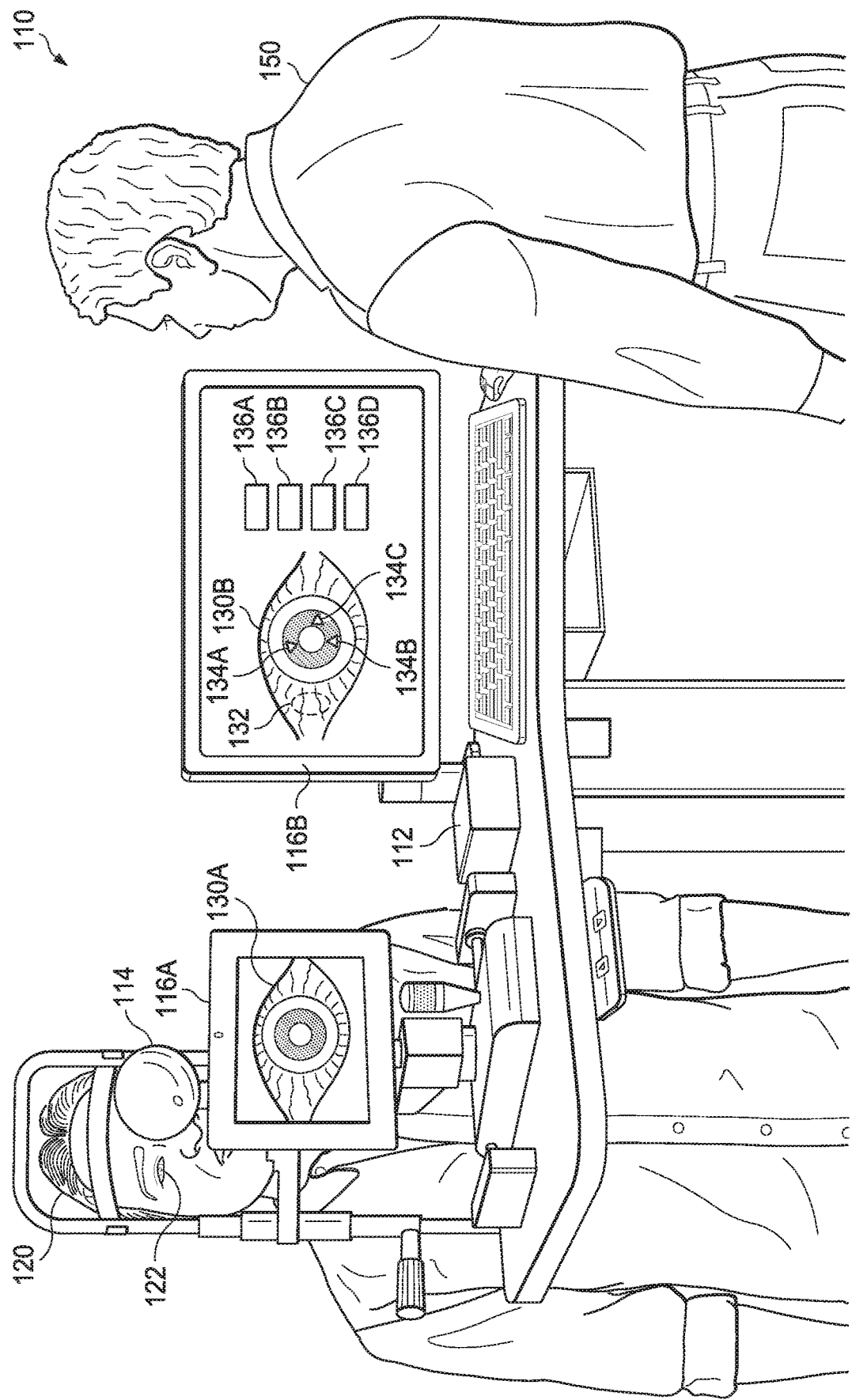
FIG. 1A illustrates an example of a medical system.

In the following description, details are set forth by way of example to facilitate discussion of the disclosed subject matter. It should be apparent to a person of ordinary skill in the field, however, that the disclosed embodiments are examples and not exhaustive of all possible embodiments.

As used herein, a reference numeral refers to a class or type of entity, and any letter following such reference numeral refers to a specific instance of a particular entity of that class or type. Thus, for example, a hypothetical entity referenced by '12A' may refer to a particular instance of a particular class/type, and the reference '12' may refer to a collection of instances belonging to that particular class/type or any one instance of that class/type in general.

Medical systems may be utilized to identify patients. In one example, a first medical system may be utilized, at a first time, in identifying a patient before a medical procedure. In another example, a second medical system may be utilized, at a second time, in identifying the patient before the medical procedure. The second time may be a later time than the first time. In one example, the first medical system may be utilized at an office of a doctor. In another example, the second medical system may be utilized at a surgical facility.

The first medical system may associate two or more identification attributes associated with the patient. For example, two or more identification attributes associated with the patient may include two or more of a name of the patient, an address of the patient, a telephone number of the patient, a government issued identification number or string of characters of the patient, a date of birth of the patient, a first medical facility identification of the patient, and a first eye identification of the patient, among others. The first eye identification of the patient may be utilized via an eye recognition process, method, and/or system to identify the patient and/or an eye of the patient.

The second medical system may associate two or more identification attributes associated with the patient. For example, two or more identification attributes associated with the patient may include two or more of the name of the patient, the address of the patient, the telephone number of the patient, the government issued identification number or string of characters of the patient, the date of birth of the patient, the first medical facility identification of the patient, a second first medical facility identification of the patient, the first eye identification of the patient, and a second eye identification of the patient, among others. The second medical system may utilize an eye recognition process, method, and/or system to obtain the second eye identification of the patient and to determine if the first eye identification of the patient and the second eye identification of the patient match. If the first eye identification of the patient and the second eye identification of the patient match, a medical procedure associated with the patient may proceed. For example, the medical procedure associated with the patient may include a surgical procedure associated with the patient.

If the first eye identification of the patient and the second eye identification of the patient match, a medical procedure may be retrieved based at least on an identification associated with the patient. The identification associated with the patient may include the first eye identification of the patient and/or the second eye identification of the patient. For example, a medical system may retrieve medical procedure information from a database. The medical system may retrieve the medical procedure information from a database based at least on the identification associated with the patient. In one example, the database may key multiple medical procedure information by identifications of patients. In another example, the database may key multiple medical procedure information by iris structures of respective eyes. Eye identifications of respective patients may include information associated with iris structures of respective one or more eyes. Eye identifications of respective patients may include information associated with one or more measurements of respective one or more eyes. The medical procedure may be automatically retrieved. For example, automatically retrieving the medical procedure may include automatically loading the medical procedure. The medical procedure may include a preplanned treatment. For example, the preplanned treatment may be automatically loaded for the matching patient and/or for the matching eye of the patient. Automatically loading the medical procedure may permit a doctor (e.g., a surgeon) to start and/or initiate the medical procedure. The medical procedure may be displayed via a microscope integrated display and/or a display of the medical system. In one example, this may reduce an amount of time for the medical procedure, compared to not automatically loading the medical procedure. In another example, this may reduce one or more possible errors in performing one or more medical procedures. If the medical procedure is automatically loaded for the doctor, based at least on an identification associated with the patient, the medical procedure may not be performed on an incorrect patient.

If the first eye identification of the patient and the second eye identification of the patient do not match, a medical procedure associated with the patient may not proceed. In one example, an error or a warning may be issued, which may alert medical personnel that the patient has not been correctly identified. In another example, an error or a warning may be issued, which may alert medical personnel that the eye of the patient has not been correctly identified.

One or more eye recognition systems, one or more eye recognition methods, and/or one or more eye recognition processes may be utilized in eye identification of a patient. For example, eye recognition may be based at least on identifying a patient by analyzing patterns based at least on one or more structures of an eye of the patient and/or one or more shapes of one or more portions of the eye of the patient. In one example, eye recognition may identify eye features via extracting landmarks and/or features from an image of the eye of the patient. In a second example, eye recognition may identify eye features via identifying one or more structures of an iris of the eye of the patient. In a third example, eye recognition may identify eye features via identifying one or more patterns of a retina of the eye of the patient. In another example, eye recognition may identify eye features via determining one or more depth measurements of the eye of the patient. A depth measurement of the eye of the patient may include a distance measurement from a cornea of the eye of the patient to a lens of the eye of the patient. A depth measurement of the eye of the patient may include a distance measurement from a lens of the eye of the patient to a retina of the eye of the patient. One or more eye recognition systems, one or more eye recognition methods, and/or one or more eye recognition processes may determine data associated with an eye of a patient. Data associated with an eye of a patient may include a template. For example, a template may be distinguished from a photograph, as a template may include data that may be utilized to distinguish an eye of a first patient from an eye of a second patient, different from the first patient.

One or more eye recognition systems, one or more eye recognition methods, and/or one or more eye recognition processes may utilize three-dimensional techniques utilizing one or more projectors and/or one or more sensors, among others, to determine information about a shape of an eye of the patient. For example, the information about the shape of the eye of the patient may be utilized to determine one or more features of a surface of the eye of the patient. The one or more features of the surface of the eye of the patient may include a contour of an eye, among others. An advantage of utilizing three-dimensional eye recognition techniques may be that three-dimensional eye recognition techniques may not be affected by changes in lighting. One or more eye recognition systems, one or more eye recognition methods, and/or one or more eye recognition processes may utilize multiple image sensors. For example, the multiple image sensors may include multiple cameras. A three-dimensional eye recognition technique may utilize multiple image sensors.

An eye recognition system may include one or more image acquisition devices. For example, the one or more image acquisition devices may include one or more cameras. An eye recognition system may include one or more light projectors. In one example, a light projector may project infrared light. In another example, a light projector may include a laser. An eye recognition system may determine locations on an eye of the patient. For example, the locations on the eye of the patient may be utilized in determining a template of the eye of the patient. The template of the eye of the patient may be associated with a topography of the eye of the patient. The template of the eye of the patient may be utilized in eye recognition. In one example, the template of the eye of the patient may be compared with another template in confirming or disaffirming an identity of the patient. In another example, the template of the eye of the patient may be compared with another template in confirming or disaffirming an identity an eye of the patient.

A medical procedure associated with the patient may include a portion of the patient (e.g., a site of the medical procedure). For example, the portion of the patient may be similar to another portion of the patient. For example, a right eye of the patient may be similar to a left eye of the patient. For example, a right eye of the patient may appear to be similar to a left eye of the patient. The medical procedure associated with the patient may be for the portion of the patient and not the other portion of the patient. For example, the medical procedure associated with the patient may be for right eye of the patient and not for the left eye of the patient. The second medical system may utilize a computer vision process, method, and/or system to determine the portion of the patient from the other portion of the patient. The computer vision process, method, and/or system may utilize an eye recognition process, method, and/or system to determine the portion of the patient from the other portion of the patient. For example, the second medical system may determine that surgical tooling equipment is within an area that is not associated with the portion of the patient. The second medical system may issue a warning or an error if the second medical system determines that surgical tooling equipment is within an area that is not associated with the portion of the patient. In one example, if the medical procedure is for the right eye of the patient (e.g., a site of the medical procedure), the second medical system may issue a warning or an error if the second medical system determines that surgical tooling equipment is within an area that is not associated with the right eye of the patient. In another, if the medical procedure is for the right eye of the patient (e.g., a site of the medical procedure), the second medical system may issue a warning or an error if the second medical system determines that surgical tooling equipment is within an area that is associated with the left eye of the patient.

Turning now to FIG. 1A, an example of a medical system is illustrated. As shown, a medical system 110 may be utilized with a patient 120. As illustrated, medical system 110 may include a computer system 112. Computer system 112 may be communicatively coupled to displays 116A and 116B. As an example, computer system 112 may be integrated with a display 116. Computer system 112 may be communicatively coupled to a biometry device 114. In one example, biometry device 114 may include one or more cameras. In another example, biometry device 114 may include a three-dimensional scanner. Biometry device 114 may be utilized in biometry of an eye 122 of patient 120. As shown, display 116A may display an image 130A associated with eye 122 of patient 120. As illustrated, display 116B may display an image 130B associated with eye 122 of patient 120.

Computer system 112 may determine eye recognition information. For example, the eye recognition information may include biometry information associated with eye 122 of patient 120. The biometry information associated with eye 122 may include one or more of a pattern of blood vessels of a sclera of eye 122, a structure of an iris of eye 122, a position of a structure of an iris of eye 122, a distance measurement of a cornea of eye 122 to a lens of eye 122, a distance measurement of a lens of eye 122 to a retina of eye 122, a corneal topography of eye 122, a retinal pattern of eye 122, a corneal thickness of eye 122, a lens thickness of eye 122, and a wavefront measurement, among others.

As shown, display 116B may display a pattern of blood vessels 132 of a sclera of eye 122. As illustrated, display 116B may display structures of an iris 134A-134C of eye 122. As shown, display 116B may display display areas 136A-136D. In one example, a display area 136 may display a distance measurement of a cornea of eye 122 to a lens of eye 122, a distance measurement of a lens of eye 122 to a retina of eye 122, a position of a structure of an iris 134, corneal topography information, or wavefront measurement information, among other biometry information associated with eye 122. In another example, a display area 136 may display any information associated with patient 120.

A person 150 may operate medical system 110. For example, person 150 may be medical personnel. Person 150 may enter identification information associated with patient 120 into computer system 112. The identification information associated with patient 120 may include one or more of a name of patient 120, an address of patient 120, a telephone number of patient 120, a government issued identification number of patient 120, a government issued identification string of patient 120, and a date of birth of patient 120, among others. In one example, computer system 112 may associate the identification information associated with patient 120 with the eye recognition information. In another example, computer system 112 may associate the identification information associated with patient 120 with a template.

Person 150 may verify one or more portions of the identification information associated with patient 120 before computer system 112 associates the identification information associated with patient 120 with the eye recognition information. For example, one or more portions of the identification information associated with patient 120 may have been stored, via a storage device accessible by computer system 112, before medical system 110 is utilized with patient 120. Person 150 may configure data associated with a portion of patient 120. For example, person 150 may configure data associated with a right eye of patient 120.

Person 150 may provide medical procedure information, associated with patient 120, to computer system 112. The medical procedure information may be associated with a medical procedure. The medical procedure information may be associated identification information associate with patient 120. Computer system 112 may store the medical procedure information. For example, computer system 112 may store the medical procedure information for later utilization. The medical procedure information may be associated with a surgery. For example, the medical procedure information may be retrieved before the surgery. The medical procedure information may be utilized during a medical procedure. For example, the medical procedure may include a surgery.

Figure 1B:
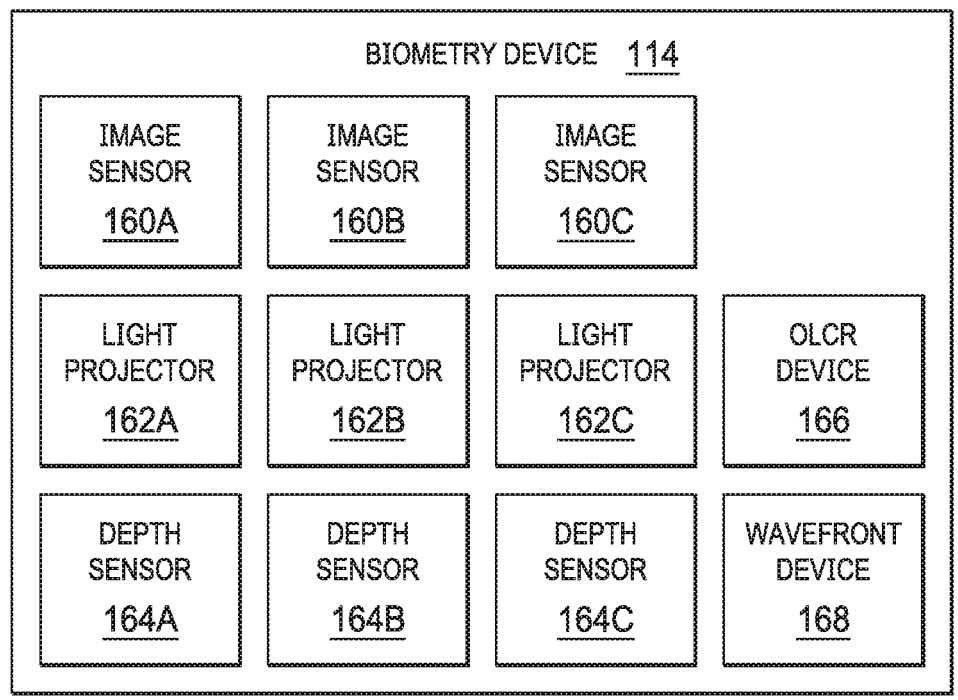
FIG. 1B illustrates an example of a biometry device.

Turning now to FIG. 1B, an example of a biometry device is illustrated. As shown, biometry device 114 may include image sensors 160A-160C. For example, an image sensor 160 may include a camera. As illustrated, biometry device 114 may include light projectors 162A-162C. In one example, a light projector 162 may project visible light. In another example, a light projector 162 may project infrared light. A light projector 162 may project circles and/or dots onto an eye of a patient. An image sensor 160 may receive reflections of the circles and/or the dots that were projected onto the eye of the patient. A computer system may determine one or more locations and/or one or more templates associated with the eye of the patient based at least on the reflections of the circles and/or the dots that were projected onto the eye of the patient. As shown, biometry device 114 may include depth sensors 164A-164C. A depth sensor 164 may include a light projector 162. A depth sensor 164 may include an optical sensor. As illustrated, biometry device 114 may include an optical low coherence reflectometer (OLCR) device 166. As shown, biometry device 114 may include a wavefront device 168.

Wavefront device 168 may include one or more of a light source and a wavefront sensor, among others. A light source may provide a first light wave to eye 122. A wavefront sensor may receive a first perturbed light wave, based at least on the first light wave, from eye 122. In one example, wavefront device 168 may determine first optical corrections based at least on the first perturbed light. In another example, a computer system may determine first optical corrections based at least on the first perturbed light. Wavefront device 168 may provide data, based at least on the first perturbed light wave, to a computer system. For example, the computer system may determine first optical corrections based at least on the data from wavefront device 168.

Any two or more of an image sensor 160, a light projector 162, a depth sensor 164, an OLCR device 166, and a wavefront device 168 may be combined. One or more of image sensors 160A-160C, one or more of light projectors 162A-162C, one or more of depth sensors 164A-164C, OLCR device 166, and/or wavefront device 168, among others, may produce data that may be utilized by a computer system.

Figure 2A:
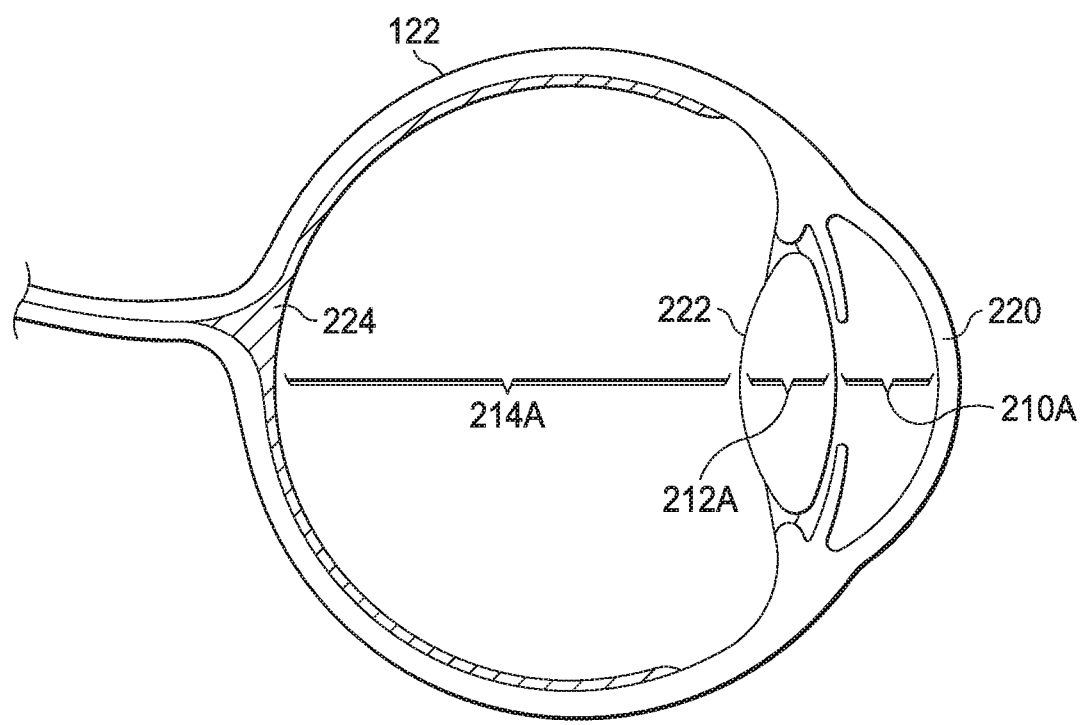
FIGS. 2A-2C illustrate examples of measurements associated with an eye.
Figure 2B:
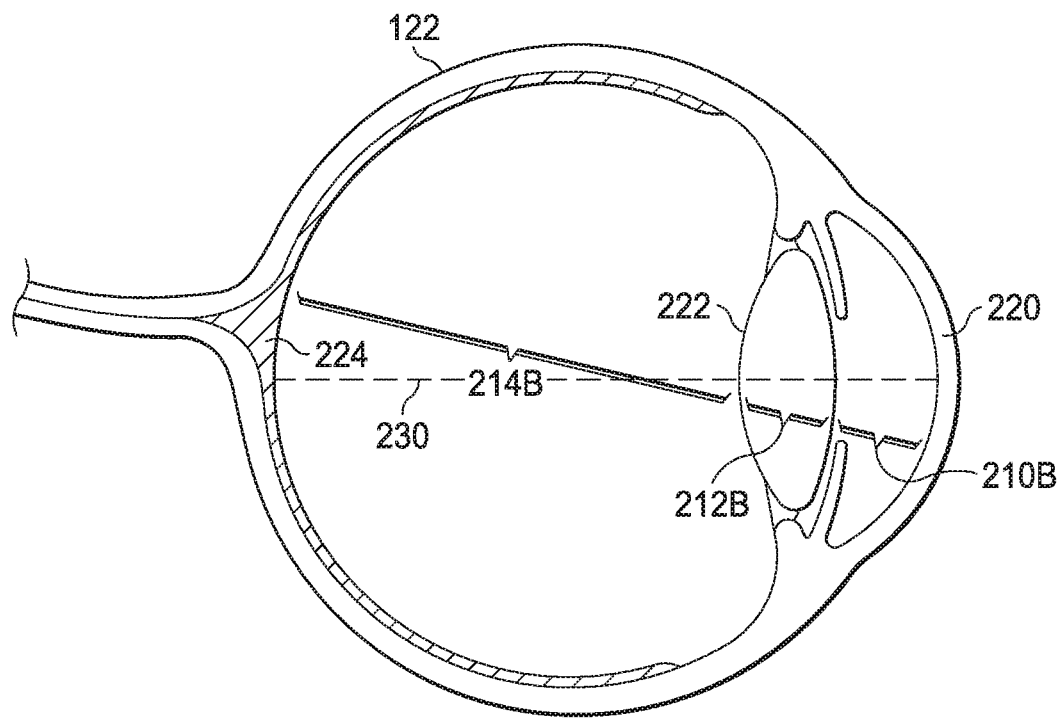
Figure 2C:
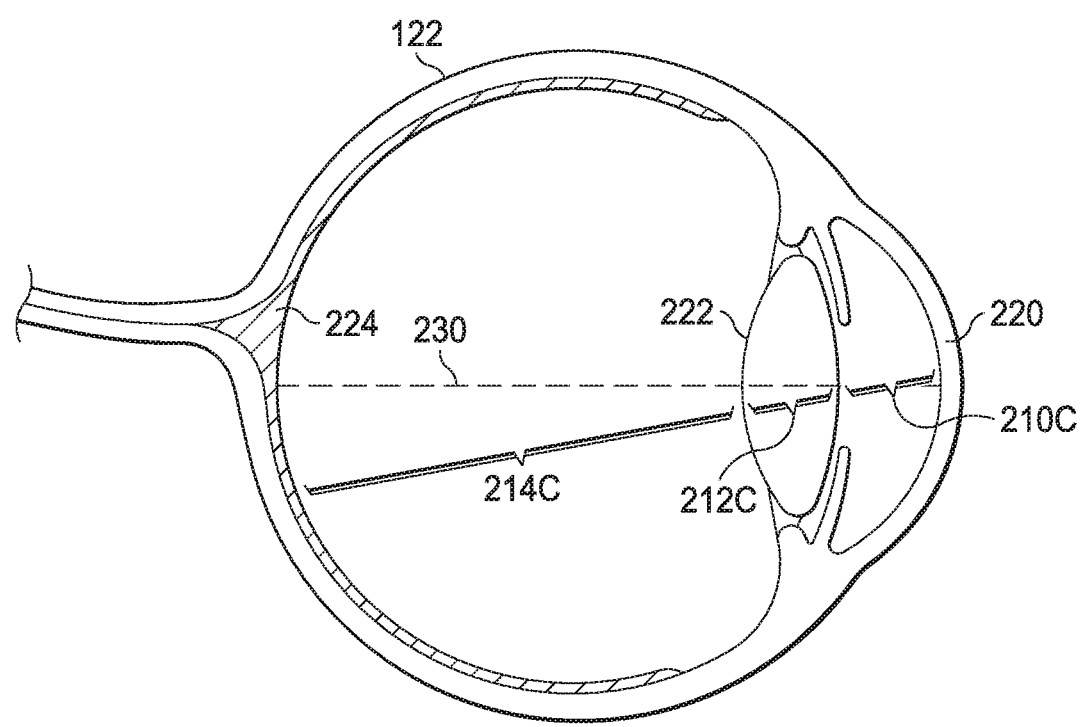

Turning now to FIGS. 2A-2C, examples of measurements associated with an eye are illustrated. As shown in FIG. 2A, measurements 210A, 212A, and 214A may be associated with eye 122. In one example, measurement 210A may be associated with a distance measurement from a cornea 220 of eye 122 to a lens 222 of eye 122. In a second example, measurement 212A may be associated with a distance measurement of lens 222 of eye 122. In another example, measurement 214A may be associated with a distance measurement from lens 222 of eye 122 to a retina 224 of eye 122. Measurements 210A, 212A, and 214A may be on axis measurements.

As illustrated in FIG. 2B, measurements 210B, 212B, and 214B may be associated with eye 122. In one example, measurement 210B may be associated with a distance measurement from cornea 220 of eye 122 to lens 222 of eye 122. In a second example, measurement 212B may be associated with a distance measurement of lens 222 of eye 122. In another example, measurement 214B may be associated with a distance measurement from lens 222 of eye 122 to retina 224 of eye 122. Measurements 210B, 212B, and 214B may be off axis measurements. For example, measurements 210B, 212B, and 214B may be off an axis 230. Measurements 210B, 212B, and 214B may be off axis 230 in a vertical direction. Measurements 210B, 212B, and 214B may be off axis 230 in a horizontal direction.

As illustrated in FIG. 2C, measurements 210C, 212C, and 214C may be associated with eye 122. In one example, measurement 210C may be associated with a distance measurement from cornea 220 of eye 122 to lens 222 of eye 122. In a second example, measurement 212C may be associated with a distance measurement of lens 222 of eye 122. In another example, measurement 214C may be associated with a distance measurement from lens 222 of eye 122 to retina 224 of eye 122. Measurements 210C, 212C, and 214C may be off axis measurements. For example, measurements 210C, 212C, and 214C may be off an axis 230. Measurements 210C, 212C, and 214C may be off axis 230 in a vertical direction. Measurements 210C, 212C, and 214C may be off axis 230 in a horizontal direction.

Biometry device 114 may perform measurements associated with eye 122. For example, biometry device 114 may determine one or more of measurements 210, 212, and 214, among others. Measurements 210, 212, and/or 214, among others, may be utilized in determining a shape of eye 122. Biometry device 114 may perform measurements associated with eye 122 without contacting eye 122. For example, biometry device 114 may determine one or more of measurements 210, 212, and 214, among others, without contacting eye 122. OLCR device 166 may determine measurements one or more of measurements 210, 212, and 214, among others, without contacting eye 122. For example, OLCR device 166 may determine one or more of measurements 210, 212, and 214, among others, utilizing a single beam interferometer or a multiple beam interferometer with a beam deflection mechanism to determine the one or more of measurements 210, 212, and 214, among others, along axis 230 (e.g., a visual axis) and/or with a number of degrees horizontally and/or vertically from axis 230.

OLCR device 166 may include the single beam interferometer or the multiple beam interferometer and/or the beam deflection mechanism. OLCR device 166 may include a light source. For example, the light source may include a diode. The diode may emit infrared light. In one example, the infrared light may be associated with a wavelength of approximately 845 nanometers (nm). In another example, the infrared light may be associated with a coherence length of approximately 30 micrometers (μm). Other light wavelengths and/or other coherence lengths may be utilized. OLCR device 166 may perform multiple scans of eye 122. For example, OLCR device 166 may perform multiple scans of eye 122 to determine each of measurements 210, 212, and 214, among others.

Figure 3A:
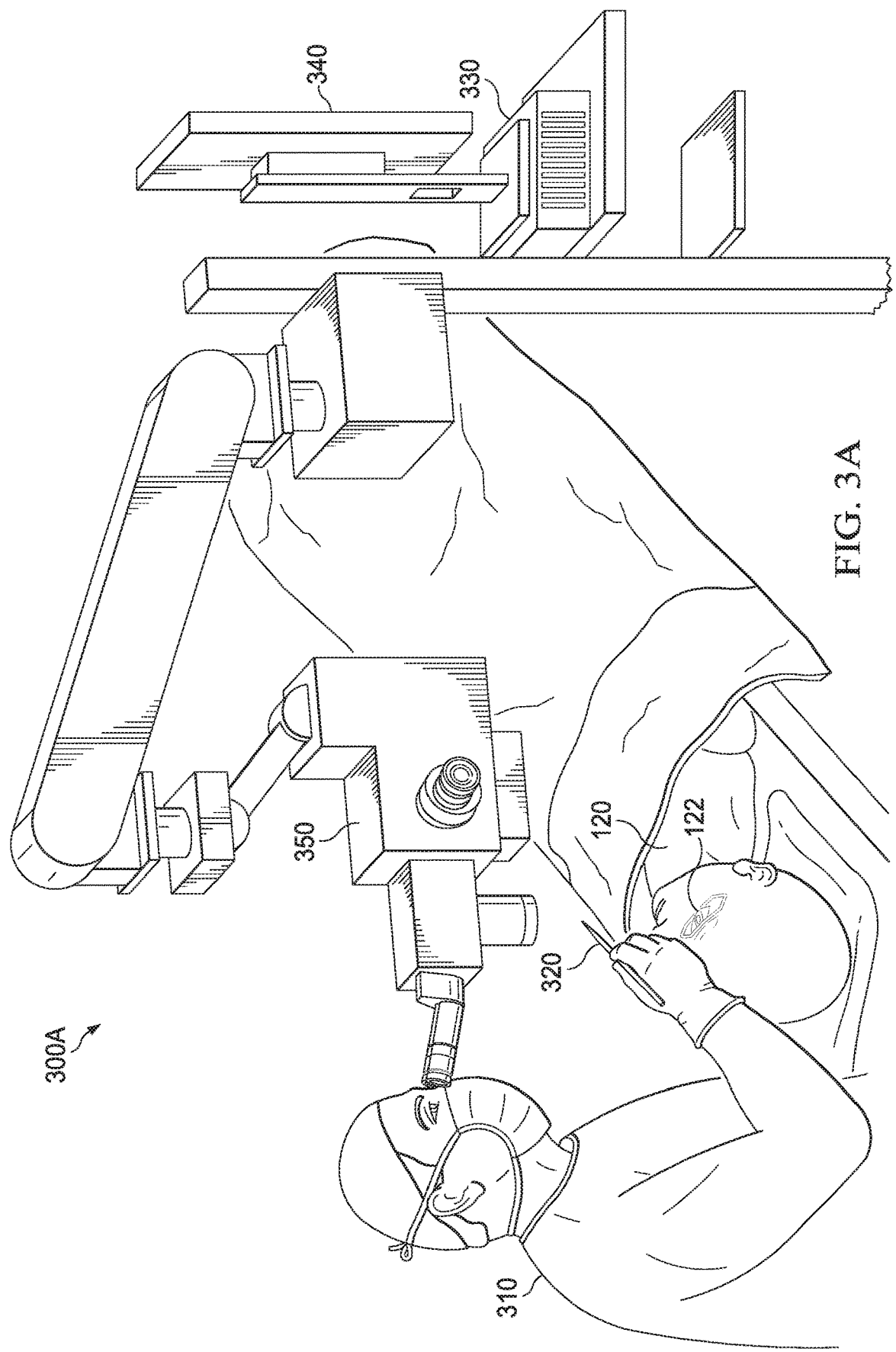
FIG. 3A illustrates a second example of a medical system.

Turning now to FIG. 3A, a second example of a medical system is illustrated. As shown, a surgeon 310 may utilize surgical tooling equipment 320. In one example, surgeon 310 may utilize surgical tooling equipment 320 in a surgery involving eye 122 of patient 120. A medical system 300A may include an ophthalmic surgical tool tracking system. As illustrated, medical system 300A may include a computer system 330, a display 340, and a microscope integrated display (MID) 350.

Computer system 330 may receive image frames captured by one or more image sensors. For example, computer system 330 may perform various image processing on the one or more image frames. Computer system 330 may perform image analysis on the one or more image frames to identify and/or extract one or more images of surgical tooling equipment 320 from the one or more image frames. Computer system 330 may generate a graphical user interface (GUI), which may overlay the one or more image frames. For example, the GUI may include one or more indicators and/or one or more icons, among others. The one or more indicators may include surgical data, such as one or more positions and/or one or more orientations. The one or more indicators may include one or more warnings. The GUI may be displayed by display 340 and/or MID 350 to surgeon 310 and/or other medical personnel.

Computer system 330, display 340, and MID 350 may be implemented in separate housings communicatively coupled to one another or within a common console or housing. A user interface may be associated with one or more of computer system 330, display 340, and MID 350, among others. For example, a user interface may include one or more of a keyboard, a mouse, a joystick, a touchscreen, an eye tracking device, a speech recognition device, a gesture control module, dials, and/or buttons, among other input devices. A user (e.g., surgeon 310 and/or other medical personnel) may enter desired instructions and/or parameters via the user interface. For example, the user interface may be utilized in controlling one or more of computer system 330, display 340, and MID 350, among others.

Figure 3B:
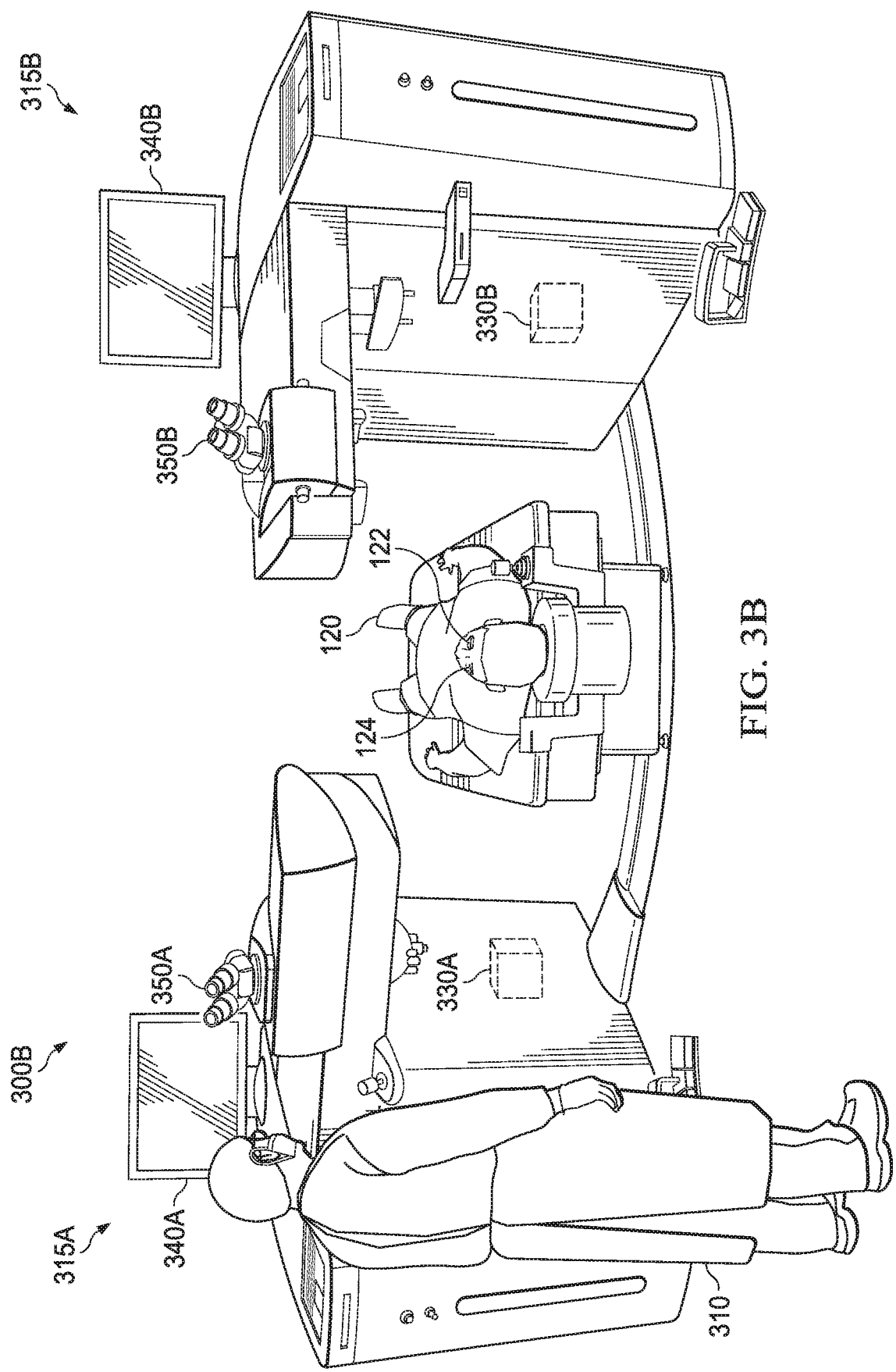
FIG. 3B illustrates another example of a medical system.

Turning now to FIG. 3B, another example of a medical system is illustrated. As shown, a surgeon 310 may utilize a system 300B. For example, surgeon 310 may utilize system 300B in a surgery involving eye 122 of patient 120. System 300B may include multiple systems. As shown, system 300B may include a cutting system 315A. For example, surgeon 310 may utilize system 315A in cutting eye 122. Eye 122 may include a flap in a cornea of an eye of patient 120. As illustrated, system 300B may include a shaping system 315B. For example, surgeon 310 may utilize shaping system 315B in performing ablation on an interior part of the cornea of patient 340.

As shown, system 315A may include a display 340A. As illustrated, system 315A may include a microscope display 350A. For example, microscope display 350A may include a MID. System 315A may include one or more of image sensors 160A-160C, one or more of light projectors 162A-162C, one or more of depth sensors 164A-164C, OLCR device 166, and/or wavefront device 168, among others. As illustrated, system 315B may include a display 340B. As shown, system 315B may include a microscope display 350B. For example, microscope display 350B may include a MID. System 315B may include one or more of image sensors 160A-160C, one or more of light projectors 162A-162C, one or more of depth sensors 164A-164C, OLCR device 166, and/or wavefront device 168, among others.

System 315A may include a laser, such as a femtosecond laser, which may use short laser pulses to ablate a series of small portions of corneal tissue to form a flap that may be lifted up to expose an interior part of the cornea. The flap may be planned and cut using one or both of cutting device displays 340A and 350A, along with control devices and a computer system 330A. As shown, system 315A may include computer system 330A. For example, computer system 330A may be coupled to one or more of image sensors 160A-160C, one or more of light projectors 162A-162C, one or more of depth sensors 164A-164C, OLCR device 166, and/or wavefront device 168, among others, of system 315A. As illustrated, system 315B may include computer system 330B. For example, computer system 330B may be coupled to one or more of image sensors 160A-160C, one or more of light projectors 162A-162C, one or more of depth sensors 164A-164C, OLCR device 166, and/or wavefront device 168, among others, of system 315B.

Systems 315A and 315B may be physically separated as shown in FIG. 3B. Patient 120 may be moved between systems 315A and 315B. Alternatively, patient 120 may remain stationary and systems 315A and 315B may be moved to patient 120. Systems 315A and 315B may be physically combined into a single unitary device, such that neither the device nor patient 120 is repositioned when switching between systems 315A and 315B.

System 300B may include one or more control devices for controlling systems 315A and 315B. For example, the one or more control devices may include one or more of an interactive display, such as a touchscreen display, a keyboard, a mouse, a touchpad, buttons, a joystick, a foot pedal, a heads-up display, and virtual-reality glasses, or other devices able to interact with a user, such as medical personnel.

System 300B may include at least one computer system configured to generate an image presented on at least one of displays 340A, 350A, 340B, and 350B, among others. For example, the at least one computer system may include one or more of computer systems 330A and 330B. One or more of computer systems 330A and 330B may be coupled to observational devices, such as a microscope, a camera, an optical coherence tomography (OCT) device or display, or another device able to measure the position of the eye undergoing surgery. One or more of computer systems 330A and 330B may be coupled to one or more of the control devices.

In one example, cutting device computer system 330A: i) may be coupled to observational devices that observe the eye when patient 120 is positioned with system 315A, ii) may provide graphical information regarding the planned flap location and the planned area of ablation to one or more of displays 340A and 350A, and iii) may be coupled to one or more control devices of system 315A. In a second example, shaping device computer 330B: i) may be coupled to observational devices that observe the eye when patient 120 is positioned with a shaping device, ii) may provide graphical information regarding the planned flap location and the planned area of ablation to one or more of displays 340B and 350B, and iii) may be coupled to one or more control devices of system 315B. In another example, a computer system may include the properties and/or the attributes described above with respect to computer systems 330A and 330B.

A computer system of a system 300 may be coupled to another part of system 300 in a wired fashion or in a wireless fashion. One of more of computer systems of system 300 may be coupled to a database, stored locally, on a remote computer system or a remote data center, or both that store patient data, treatments plans, and/or other information associated with medical treatments and/or system 300. In one example, the database may include a relational database. In a second example, the database may include a graph database. In another example, the database may include a "Not Only SQL" (NoSQL) database.

System 300 may enter information regarding a patient and the treatment to be performed on that patient or actually performed on that patient. System 300 may allow a user to enter and view information regarding a patient and the treatment to be performed on that patient. Such data may include information about the patient, such as identifying information, the patient's medical history, and information about eye 122 being treated. Such data may include information about the treatment plans, such as the shape and location of a corneal cut and a shape and location of ablation, among others.

Figure 3C:
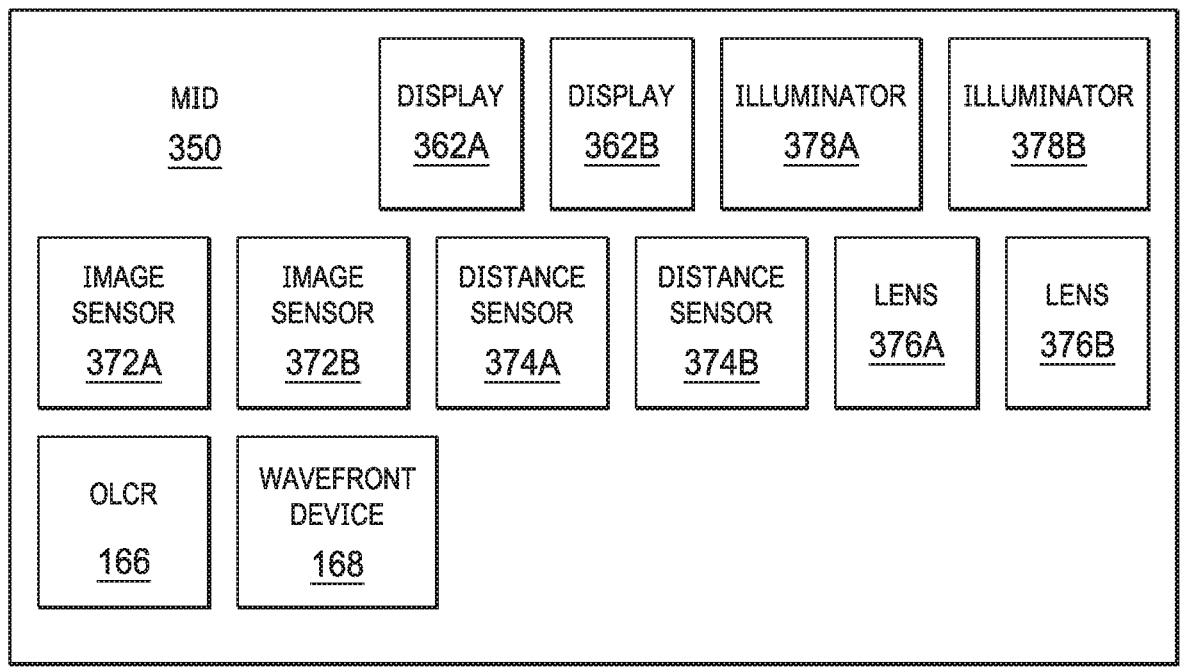
FIG. 3C illustrates an example of a microscope integrated display and examples of surgical tooling equipment.
Figure 3C:
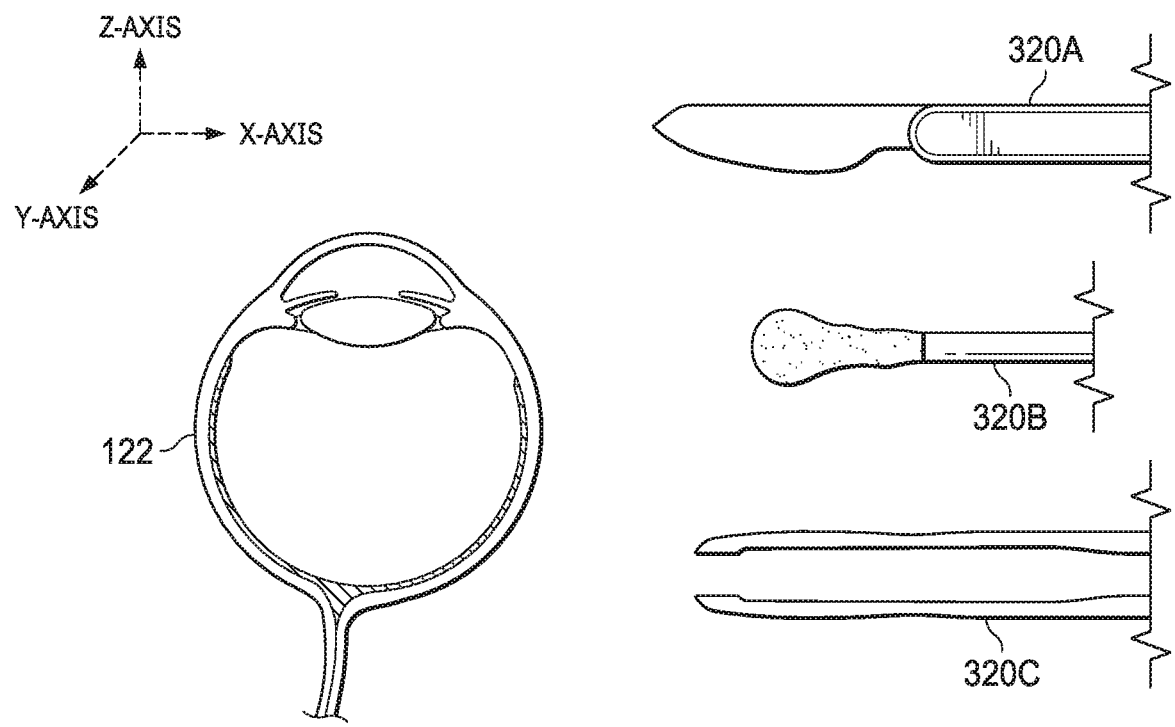

Turning now to FIG. 3C, an example of a microscope integrated display and examples of surgical tooling equipment are illustrated. As shown, surgical tooling equipment 320A may be or include a scalpel. As illustrated, surgical tooling equipment 320B may be or include a Q-tip. As shown, surgical tooling equipment 320C may be or include tweezers. Other surgical tooling equipment that is not specifically illustrated may be utilized with one or more systems, one or more processes, and/or one or more methods described herein.

As an example, surgical tooling equipment 320 may be marked with one or more patterns. The one or more patterns may be utilized in identifying surgical tooling equipment 320. The one or more patterns may include one or more of a hash pattern, a stripe pattern, and a fractal pattern, among others. As another example, surgical tooling equipment 320 may be marked with a dye and/or a paint. The dye and/or the paint may reflect one or more of visible light, infrared light, and ultraviolet light, among others. In one example, an illuminator 378 may provide ultraviolet light, and image sensor 372 may receive the ultraviolet light reflected from surgical tooling equipment 320. Computer system 330 may receive image data, based at least on the ultraviolet light reflected from surgical tooling equipment 320, from image sensor 372 and may utilize the image data, based at least on the ultraviolet light reflected from surgical tooling equipment 320, to identify surgical tooling equipment 320 from other image data provided by image sensor 372. In another example, an illuminator 378 may provide infrared light, and image sensor 372 may receive the infrared light reflected from surgical tooling equipment 320. Computer system 330 may receive image data, based at least on the infrared light reflected from surgical tooling equipment 320, from image sensor 372 and may utilize the image data, based at least on the infrared light reflected from surgical tooling equipment 320, to identify surgical tooling equipment 320 from other image data provided by image sensor 372.

As illustrated, MID 350 may include displays 362A and 362B. For example, surgeon 310 may look into multiple eye pieces, and displays 362A and 362B may display information to surgeon 310. Although MID 350 is shown with multiple displays, MID 350 may include a single display 362. For example, MID 350 may be implemented with one or more displays 362. As shown, MID 350 may include image sensors 372A and 372B. In one example, image sensors 372A and 372B may acquire images. In a second example, image sensors 372A and 372B may include cameras. In another example, an image sensor 372 may acquire images via one or more of visible light, infrared light, and ultraviolet light, among others. One or more image sensors 372A and 372B may provide data of images to computer system 330. Although MID 350 is shown with multiple image sensors, MID 350 may include a single image sensor 372. For example, MID 350 may be implemented with one or more image sensors 372.

As illustrated, MID 350 may include distance sensors 374A and 374. For example, a distance sensor 374 may determine a distance to surgical tooling equipment 320. Distance sensor 374 may determine a distance associated with a Z-axis. Although MID 350 is shown with multiple image sensors, MID 350 may include a single distance sensor 374. In one example, MID 350 may be implemented with one or more distance sensors 374. In another example, MID 350 may be implemented with no distance sensor. As shown, MID 350 may include lenses 376A and 376B. Although MID 350 is shown with multiple lenses 376A and 376B, MID 350 may include a single lens 376. For example, MID 350 may be implemented with one or more lenses 376. As illustrated, MID 350 may include illuminators 378A and 378B. For example, an illuminator 378 may provide and/or produce one or more of visible light, infrared light, and ultraviolet light, among others. Although MID 350 is shown with multiple illuminators, MID 350 may include a single illuminator 378. For example, MID 350 may be implemented with one or more illuminators 378. MID 350 may include one or more structures and/or one or more functionalities as those described with reference to biometry device 114. In one example, MID 350 may include OLCR device 166. In another example, MID 350 may include wavefront device 168.

System 300 may identify a patient. For example, system 300 may identify patient 120. System 300 may identify a patient to avoid a performance of an incorrect medical procedure to the patient. For example, system 300 may identify the patient to avoid a performance of a medical procedure, which was designated for another patient, to the patient.

Figure 4A:
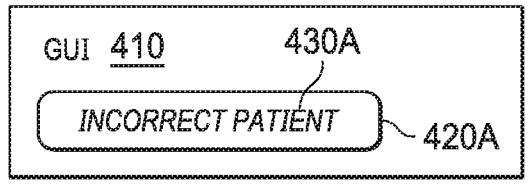
FIG. 4A illustrates an example of a graphical user interface that provides a warning or an error.
Figure 4B:
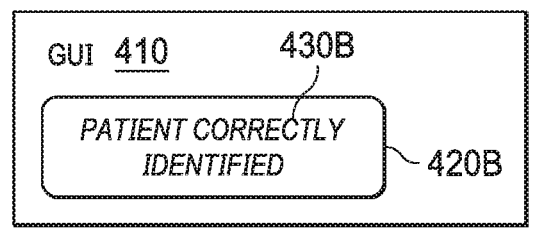
FIG. 4B illustrates an example of a graphical user interface that provides an indication that a patient has been correctly identified.

A GUI 410, illustrated in FIG. 4A, may provide a warning or an error that an incorrect patient has been identified. In one example, the warning or the error may include an icon 420A. In a second example, the warning or the error may include text 430A, which may indicate that an incorrect patient has been detected. GUI 410 may be displayed via display 340 and/or MID 350. In another example, the warning or the error may include one or more audible sounds. GUI 410, illustrated in FIG. 4B, may provide the indication that the patient has been correctly identified. In one example, the indication may include an icon 420B. In another example, the indication may include text 430B, which may indicate that the patient has been correctly identified. GUI 410 may be displayed via display 340 and/or MID 350.

System 300 may identify an eye of a patient. In one example, system 300 may identify eye 122. In another example, system 300 may identify eye 124. System 300 may not identify an eye of a patient. In one example, if system 300 does not identify an eye of a patient, system 300 may provide information that indicates that the eye of the patient was not identified. In a second example, if system 300 does not identify an eye of a patient, system 300 may deny access of one or more portions of system 300. In another example, if system 300 does not identify an eye of a patient, system 300 may deny access of one or more functionalities of system 300.

Figure 4C:
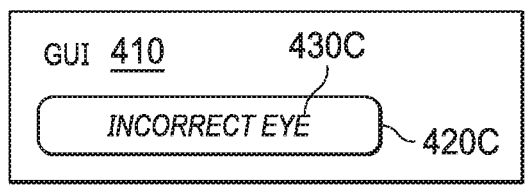
FIG. 4C illustrates another example of a graphical user interface that provides a warning or an error.
Figure 4D:
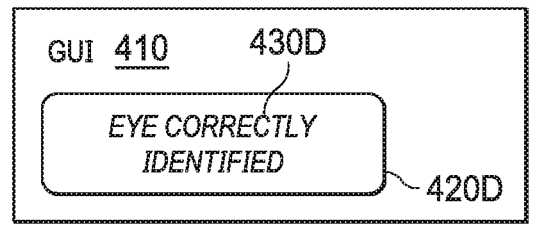
FIG. 4D illustrates an example of a graphical user interface that provides an indication that an eye of a patient has been correctly identified.

GUI 410, illustrated in FIG. 4C, may provide a warning or an error that an incorrect eye has been identified. In one example, the warning or the error may include an icon 420C. In a second example, the warning or the error may include text 430C, which may indicate that an incorrect eye has been detected. GUI 410 may be displayed via display 340 and/or MID 350. In another example, the warning or the error may include one or more audible sounds. GUI 410, illustrated in FIG. 4D, may provide an indication that the eye has been correctly identified. In one example, the indication may include an icon 420D. In another example, the indication may include text 430D, which may indicate that the eye has been correctly identified. GUI 410 may be displayed via display 340 and/or MID 350.

System 300 may repeat identifying an eye of a patient. In one example, system 300 may identify an eye of patient 120 when surgeon 310 performs at least a first portion of a medical procedure utilizing system 315A. In another example, system 300 may identify an eye of patient 120 when surgeon 310 performs at least a second portion of the medical procedure utilizing system 315B. The medical procedure may be for eye 122. In one example, the first portion of the medical procedure may be performed utilizing system 315A. In another example, the second portion of the medical procedure may be performed utilizing system 315B. System 300 may determine if eye 122 is identified before the second portion of the medical procedure is to be performed utilizing system 315B. For example, system 300 may determine if eye 122 is identified before the second portion of the medical procedure is to be performed utilizing system 315B so that the second portion of the medical procedure may not be performed on eye 124.

Figure 5A:
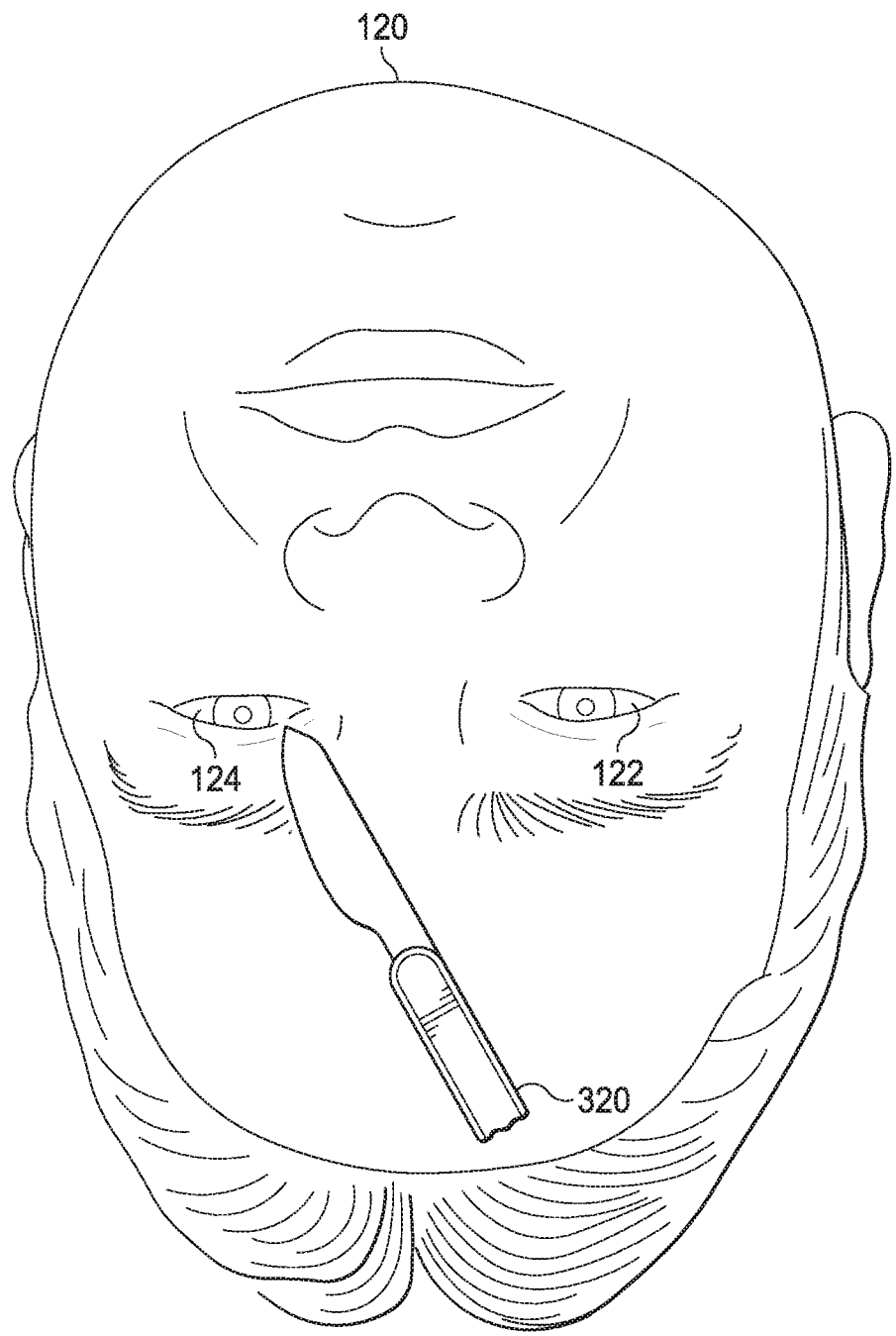
FIG. 5A illustrates an example of surgical tooling equipment proximate to an incorrect eye.
Figure 5B:
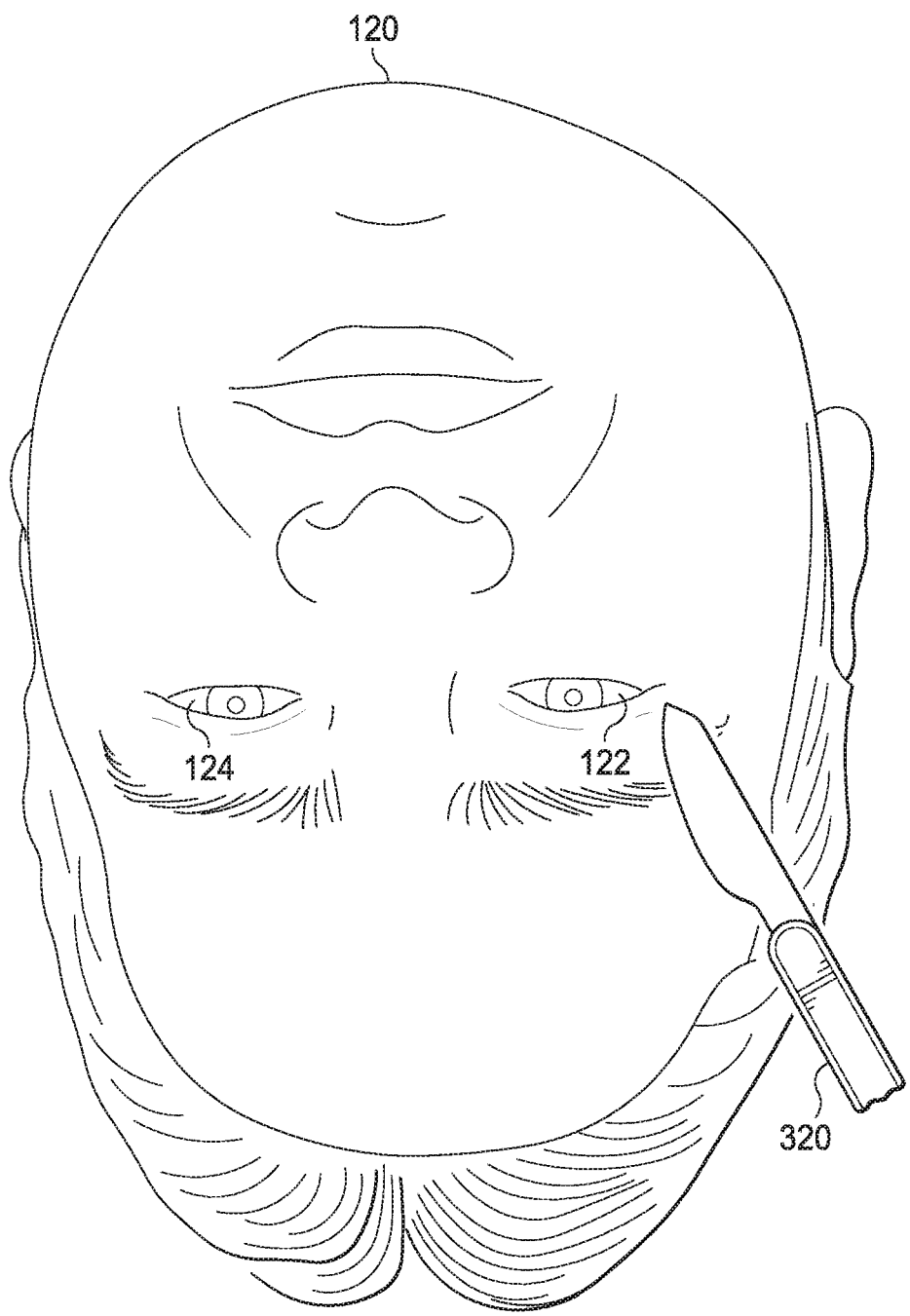
FIG. 5B illustrates an example of surgical tooling equipment proximate to a correct eye.

System 300 may determined if surgical tooling equipment is utilized with a correct eye during a medical procedure (e.g., a surgical procedure). In one example, system 300 may determine that surgical tooling equipment 320 may not be utilized on eye 124, as illustrated in FIG. 5A. System 300 may identify eye 124 and may determine that surgical tooling equipment 320 may not be utilized with eye 124. System 300 may not identify an eye and may determine that surgical tooling equipment 320 may not be utilized with the eye that was not identified. In another example, system 300 may determine that surgical tooling equipment 320 may be utilized with eye 122, as illustrated in FIG. 5B. System 300 may identify eye 122 and may determine that surgical tooling equipment 320 may be utilized with eye 122.

Figure 5C:
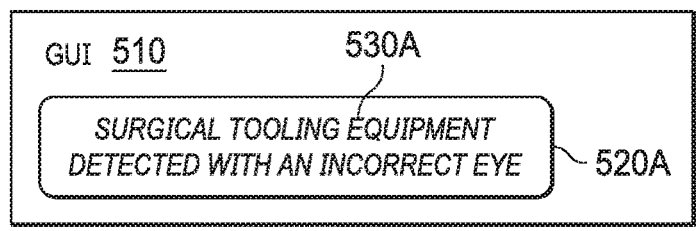
FIG. 5C illustrates another example of a graphical user interface that provides a warning or an error.

A GUI 510, illustrated in FIG. 5C, may provide a warning that surgical tooling equipment 320 is not to be utilized with an incorrect eye. In one example, the warning may include an icon 520A. In a second example, the warning may include text 530A, which may indicate that surgical tooling equipment 320 has been detected in an incorrect eye. GUI 510 may be displayed via display 340 and/or MID 350. A warning that surgical tooling equipment 320 is not to be utilized with an incorrect eye may include one or more audible sounds.

Figure 5D:
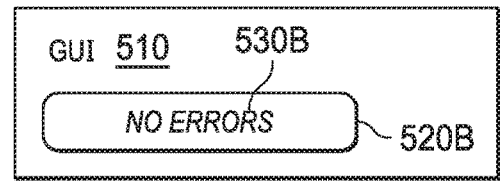
FIG. 5D illustrates an example of a graphical user interface that provides an indication that no errors have been identified.

GUI 510, illustrated in FIG. 5D, may provide an indication that surgical tooling equipment 320 may be utilized with eye 122. In one example, the indication may include an icon 520B. In another example, the indication may include text 530B, which may indicate that no errors have been detected. GUI 510 may be displayed via display 340 and/or MID 350.

Figure 6:
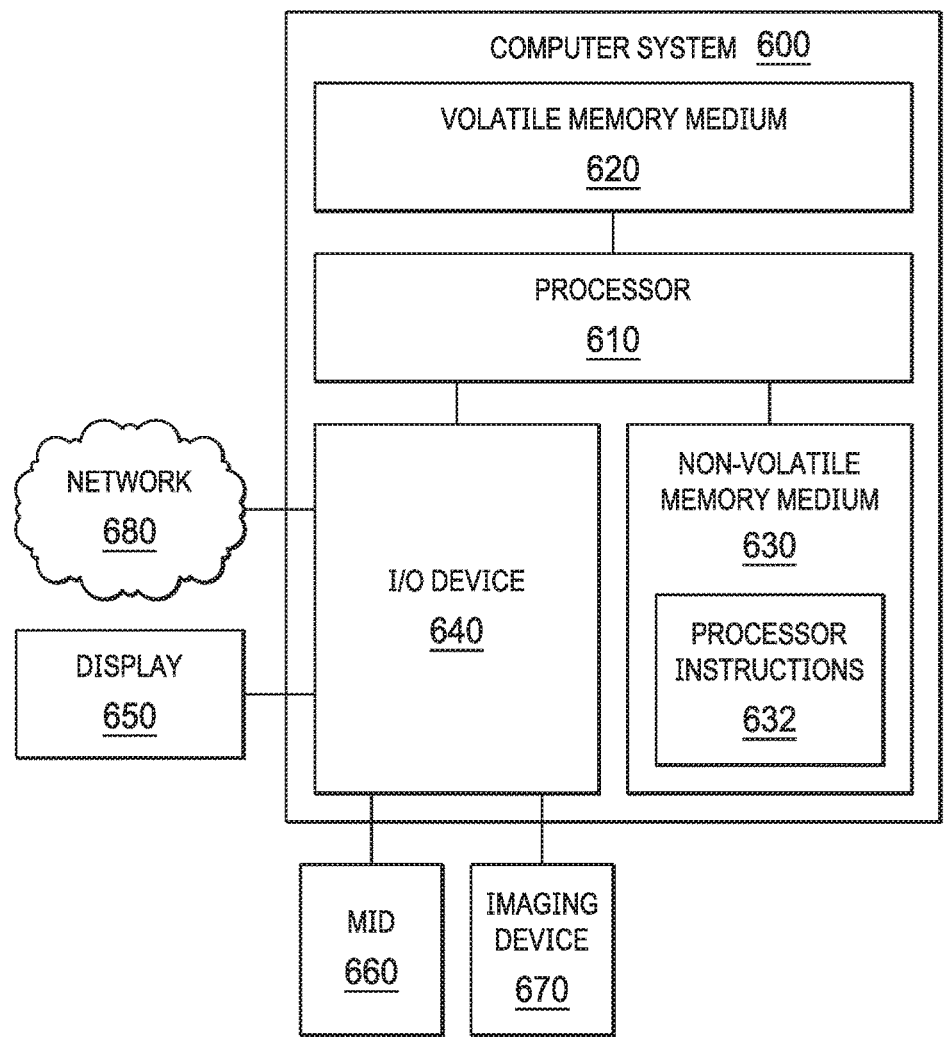
FIG. 6 illustrates an example of a computer system.

Turning now to FIG. 6, an example of a computer system is illustrated. As shown, a computer system 600 may include a processor 610, a volatile memory medium 620, a non-volatile memory medium 630, and an input/output (I/O) device 640. As illustrated, volatile memory medium 620, non-volatile memory medium 630, and I/O device 640 may be communicatively coupled to processor 610.

The term "memory medium" may mean a "memory", a "storage device", a "memory device", a "computer-readable medium", and/or a "tangible computer readable storage medium". For example, a memory medium may include, without limitation, storage media such as a direct access storage device, including a hard disk drive, a sequential access storage device, such as a tape disk drive, compact disk (CD), random access memory (RAM), read-only memory (ROM), CD-ROM, digital versatile disc (DVD), electrically erasable programmable read-only memory (EEPROM), flash memory, non-transitory media, and/or one or more combinations of the foregoing. As shown, non-volatile memory medium 630 may include processor instructions 632. Processor instructions 632 may be executed by processor 610. In one example, one or more portions of processor instructions 632 may be executed via non-volatile memory medium 630. In another example, one or more portions of processor instructions 632 may be executed via volatile memory medium 620. One or more portions of processor instructions 632 may be transferred to volatile memory medium 620.

Processor 610 may execute processor instructions 632 in implementing at least a portion of one or more systems, one or more flow charts, one or more processes, and/or one or more methods described herein. For example, processor instructions 632 may be configured, coded, and/or encoded with instructions in accordance with at least a portion of one or more systems, one or more flowcharts, one or more methods, and/or one or more processes described herein. Although processor 610 is illustrated as a single processor, processor 610 may be or include multiple processors. One or more of a storage medium and a memory medium may be a software product, a program product, and/or an article of manufacture. For example, the software product, the program product, and/or the article of manufacture may be configured, coded, and/or encoded with instructions, executable by a processor, in accordance with at least a portion of one or more systems, one or more flowcharts, one or more methods, and/or one or more processes described herein.

Processor 610 may include any suitable system, device, or apparatus operable to interpret and execute program instructions, process data, or both stored in a memory medium and/or received via a network. Processor 610 further may include one or more microprocessors, microcontrollers, digital signal processors (DSPs), application specific integrated circuits (ASICs), or other circuitry configured to interpret and execute program instructions, process data, or both.

I/O device 640 may include any instrumentality or instrumentalities, which allow, permit, and/or enable a user to interact with computer system 600 and its associated components by facilitating input from a user and output to a user. Facilitating input from a user may allow the user to manipulate and/or control computer system 600, and facilitating output to a user may allow computer system 600 to indicate effects of the user's manipulation and/or control. For example, I/O device 640 may allow a user to input data, instructions, or both into computer system 600, and otherwise manipulate and/or control computer system 600 and its associated components. I/O devices may include user interface devices, such as a keyboard, a mouse, a touch screen, a joystick, a handheld lens, a tool tracking device, a coordinate input device, or any other I/O device suitable to be used with a system.

I/O device 640 may include one or more busses, one or more serial devices, and/or one or more network interfaces, among others, that may facilitate and/or permit processor 610 to implement at least a portions of one or more systems, processes, and/or methods described herein. In one example, I/O device 640 may include a storage interface that may facilitate and/or permit processor 610 to communicate with an external storage. The storage interface may include one or more of a universal serial bus (USB) interface, a SATA (Serial ATA) interface, a PATA (Parallel ATA) interface, and a small computer system interface (SCSI), among others. In a second example, I/O device 640 may include a network interface that may facilitate and/or permit processor 610 to communicate with a network. I/O device 640 may include one or more of a wireless network interface and a wired network interface. In a third example, I/O device 640 may include one or more of a peripheral component interconnect (PCI) interface, a PCI Express (PCIe) interface, a serial peripheral interconnect (SPI) interface, and an inter-integrated circuit ($I^2C$) interface, among others. In a fourth example, I/O device 640 may include circuitry that may permit processor 610 to communicate data with one or more sensors. In a fifth example, I/O device 640 may facilitate and/or permit processor 610 to communicate data with one or more of a display 650 and a MID 660, among others. In another example, I/O device 640 may facilitate and/or permit processor 610 to communicate data with an imaging device 670. As illustrated, I/O device 640 may be coupled to a network 680. For example, I/O device 640 may include a network interface.

Network 680 may include a wired network, a wireless network, an optical network, or a combination of the foregoing, among others. Network 680 may include and/or be coupled to various types of communications networks. For example, network 680 may include and/or be coupled to a local area network (LAN), a wide area network (WAN), an Internet, a public switched telephone network (PSTN), a cellular telephone network, a satellite telephone network, or a combination of the foregoing, among others. A WAN may include a private WAN, a corporate WAN, a public WAN, or a combination of the foregoing, among others.

A computer system described herein may include one or more structures and/or one or more functionalities as those described with reference to computer system 600. In one example, computer system 112 may include one or more structures and/or one or more functionalities as those described with reference to computer system 600. In a second example, computer system 330 may include one or more structures and/or one or more functionalities as those described with reference to computer system 600. In another example, a computer system of MID 350 may include one or more structures and/or one or more functionalities as those described with reference to computer system 600.

Figure 7B:
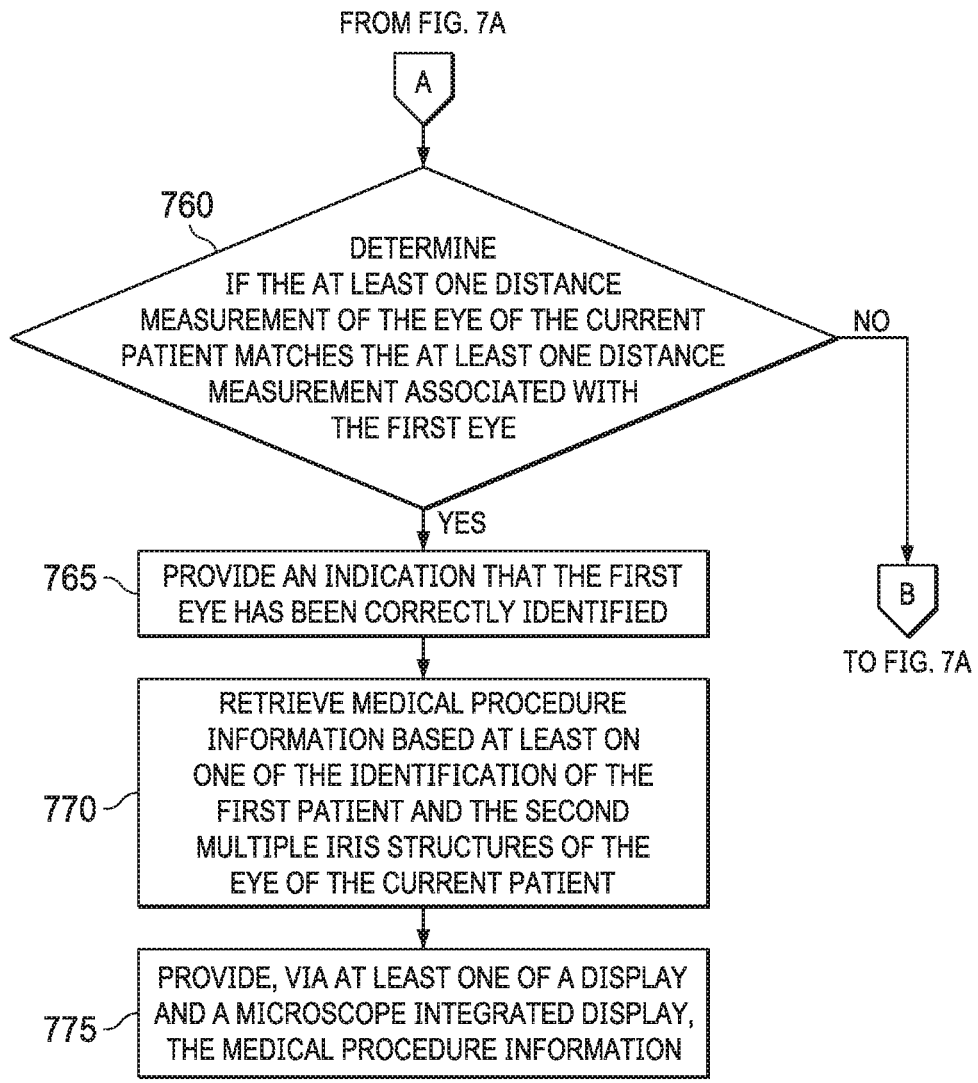

Turning now to FIGS. 7A and 7B, an example of a method of operating a medial system is illustrated. At 710, an identification of a first patient may be received. For example, computer system 330 may receive an identification of a first patient. The first patient may be patient 120. The identification of the first patient may include a name of the first patient. The identification of the first patient may include a number or a string of characters associated with the first patient.

Figure 8A:
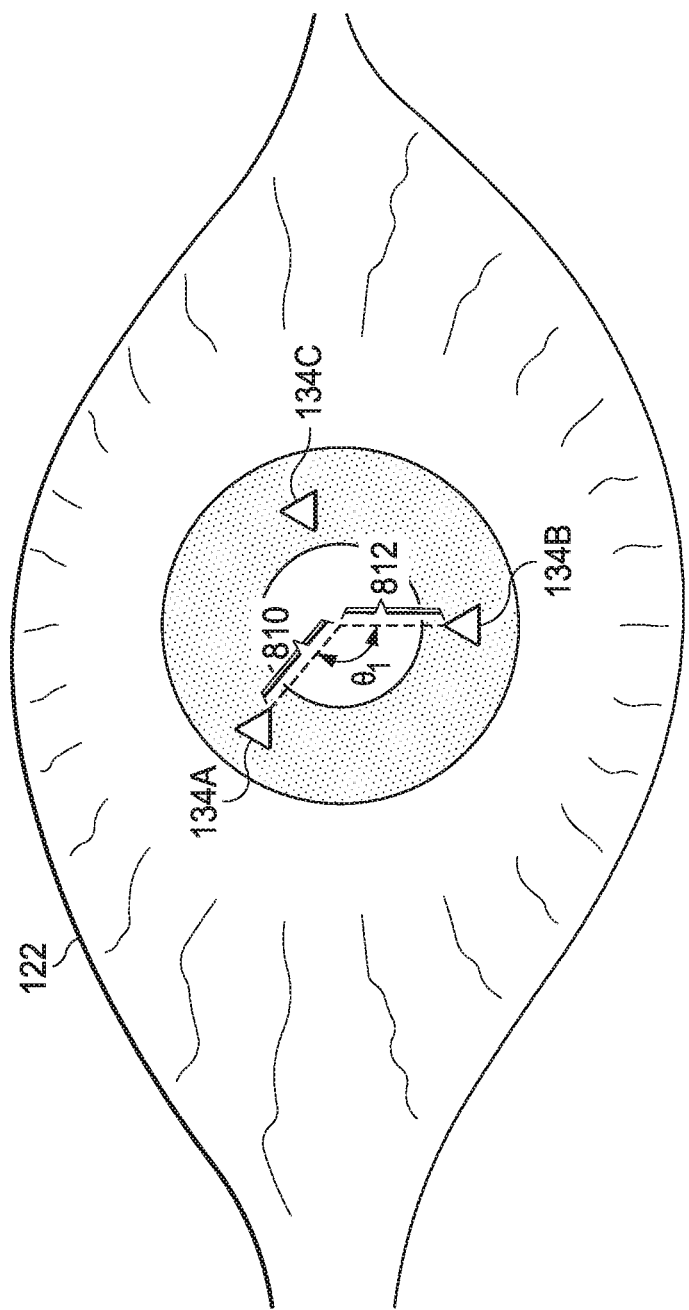
FIGS. 8A and 8B illustrate examples of measurements of structures of an iris of an eye of a patient.
Figure 8B:
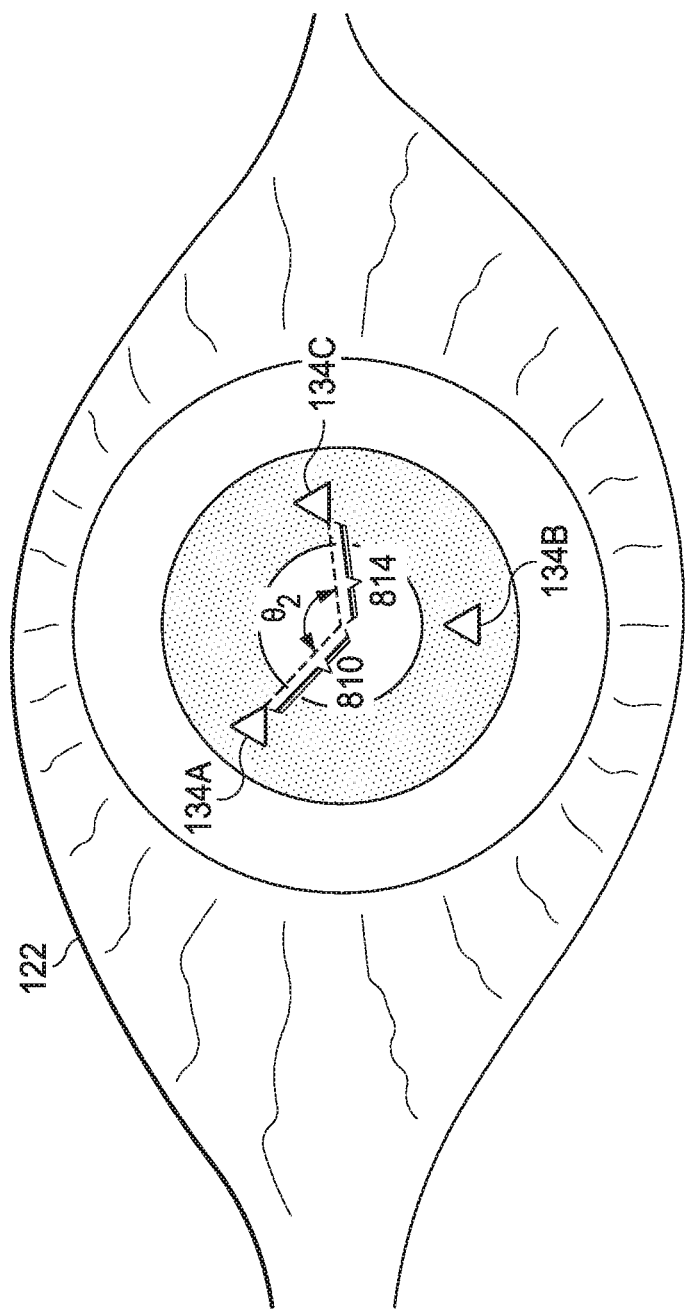

At 715, first eye identification information that includes first multiple iris structures associated with a first eye of the first patient may be retrieved based at least on the identification of the first patient. For example, the first multiple iris structures may include multiple of iris structures 134A-134C. The first eye identification information may include pattern of blood vessels 132. The first eye identification information may include one or more of measurements 210A, 212A, 214A, 210B, 212B, 214B, 210C, 212C, and 214C, among others. The first eye identification information may include one or more of measurements 810-814, among others, illustrated in FIGS. 8A and 8B. The first eye identification information may include one or more of measurements $\theta_1$ and $\theta_2$, among others, illustrated in FIGS. 8A and 8B. For example, measurements $\theta_1$ and $\theta_2$ may be angular measurements. An angular measurement may be measured in degrees, radians, etc.

At 720, second multiple iris structures of an eye of a current patient may be determined. In one example, an eye of a current patient may be an eye 822, illustrated in FIGS. 8C and 8D. Multiple of iris structures 834A-834C of eye 822 may be determined. In another example, an eye of a current patient may be an eye 824, illustrated in FIGS. 8E and 8F. Multiple of iris structures 836A-836C of eye 824 may be determined.

At 725, at least one distance measurement of the eye of the current patient may be determined. In one example, the at least one distance measurement of the eye of the current patient may include a distance measurement 850A from a cornea 860 of eye 822 to a lens 862 of eye 822, as illustrated in FIG. 8G. In a second example, the at least one distance measurement of the eye of the current patient may include a distance measurement 852A of lens 862, as illustrated in FIG. 8G. In a third example, the at least one distance measurement of the eye of the current patient may include a distance measurement 854A from lens 862 of eye 822 to a retina 864 of eye 822. Measurements 850A, 852A, and 854A may be on axis measurements.

Figure 8C:
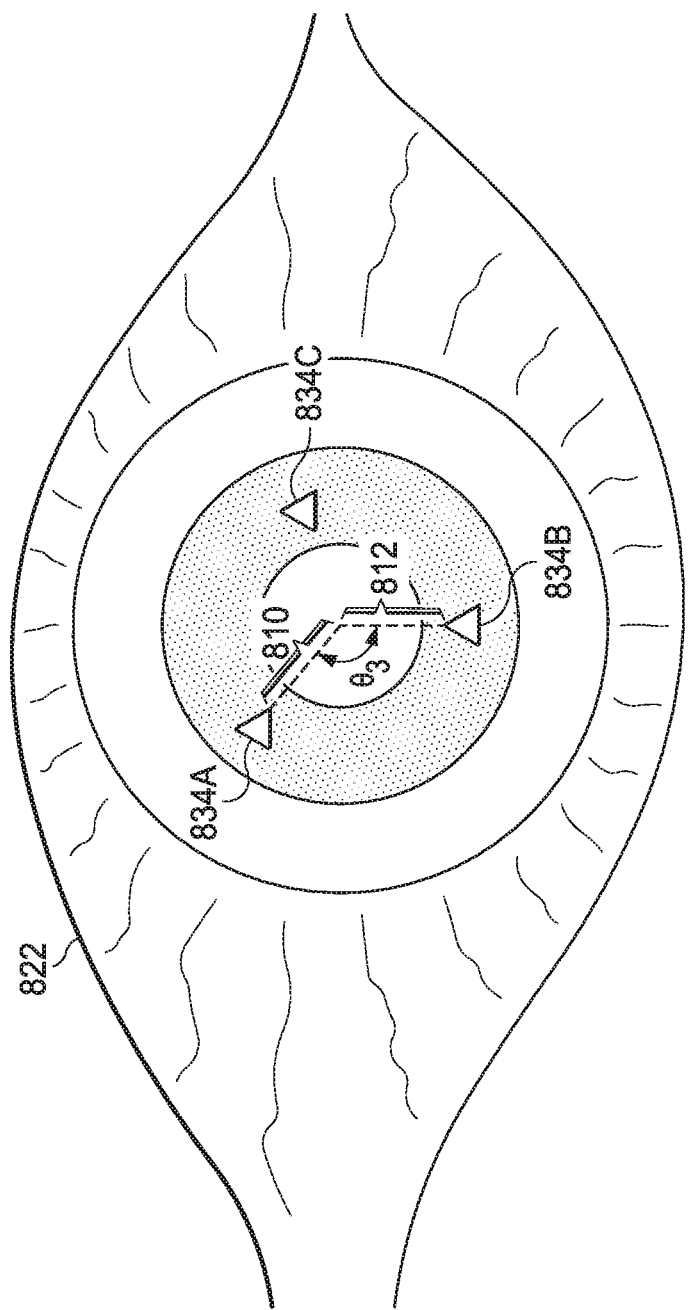
FIGS. 8C and 8D illustrate examples of measurements of structures of an iris of an eye of a current patient.
Figure 8D:
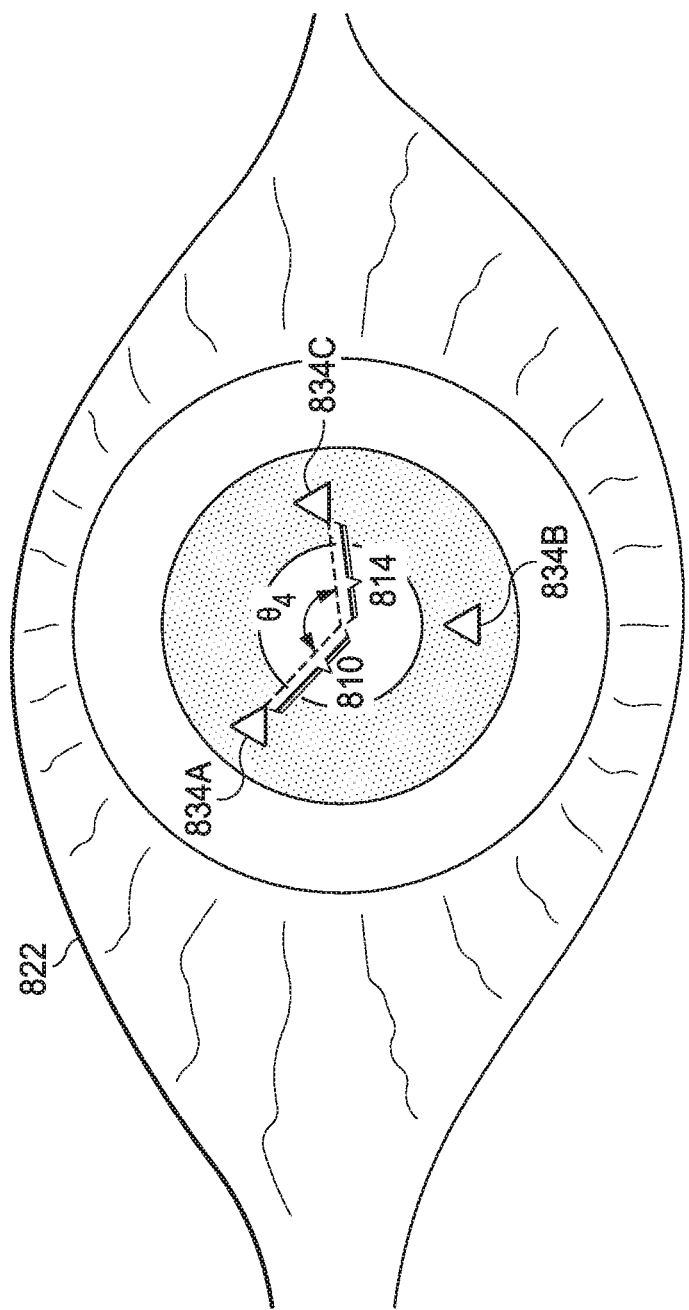
Figure 8F:
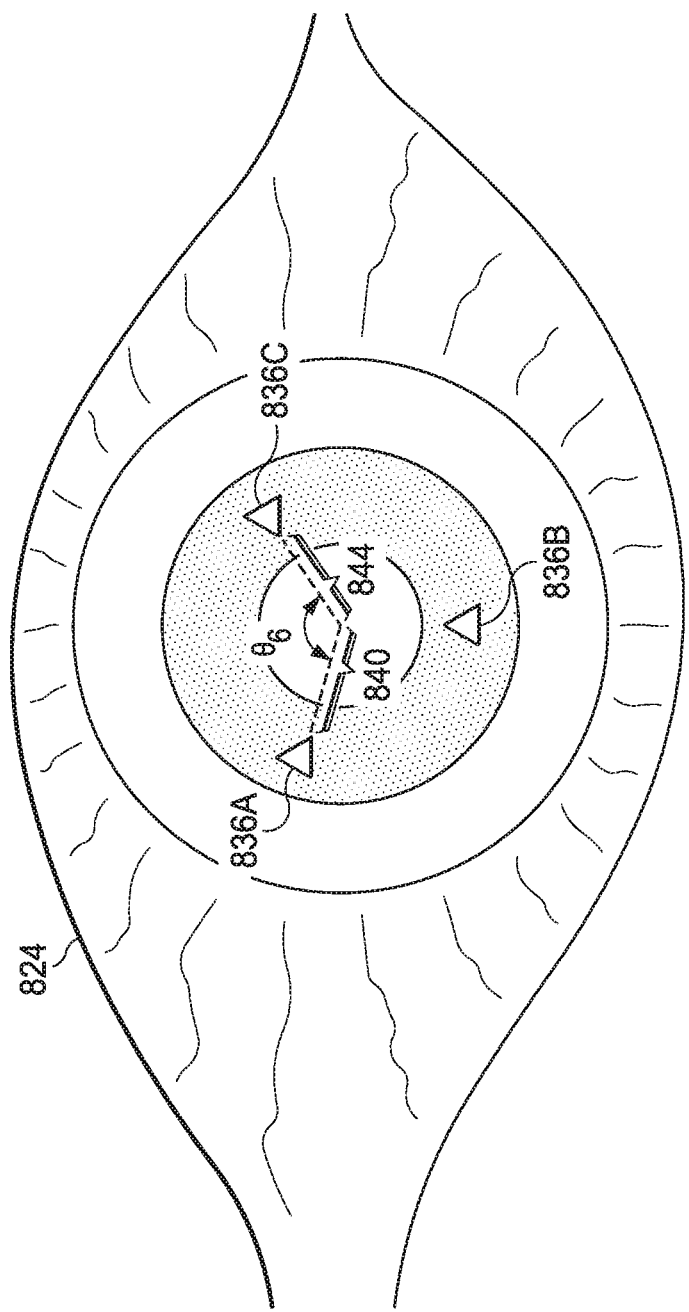
Figure 8G:
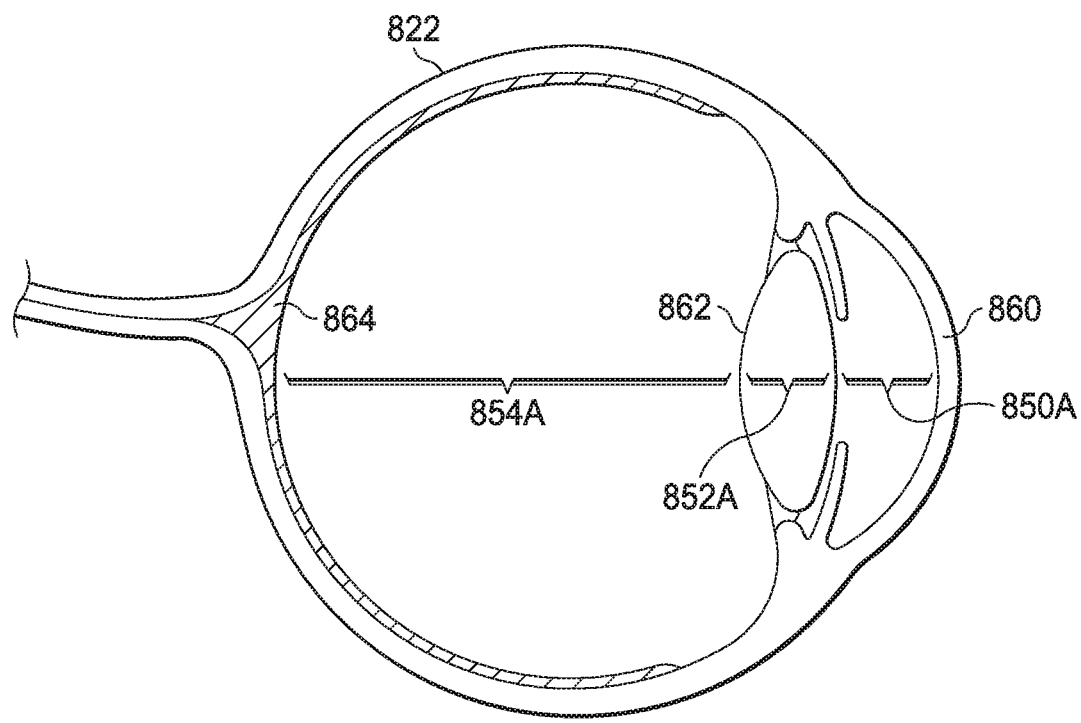
FIGS. 8G-8I illustrate examples of measurements of an eye of a current patient.
Figure 8H:
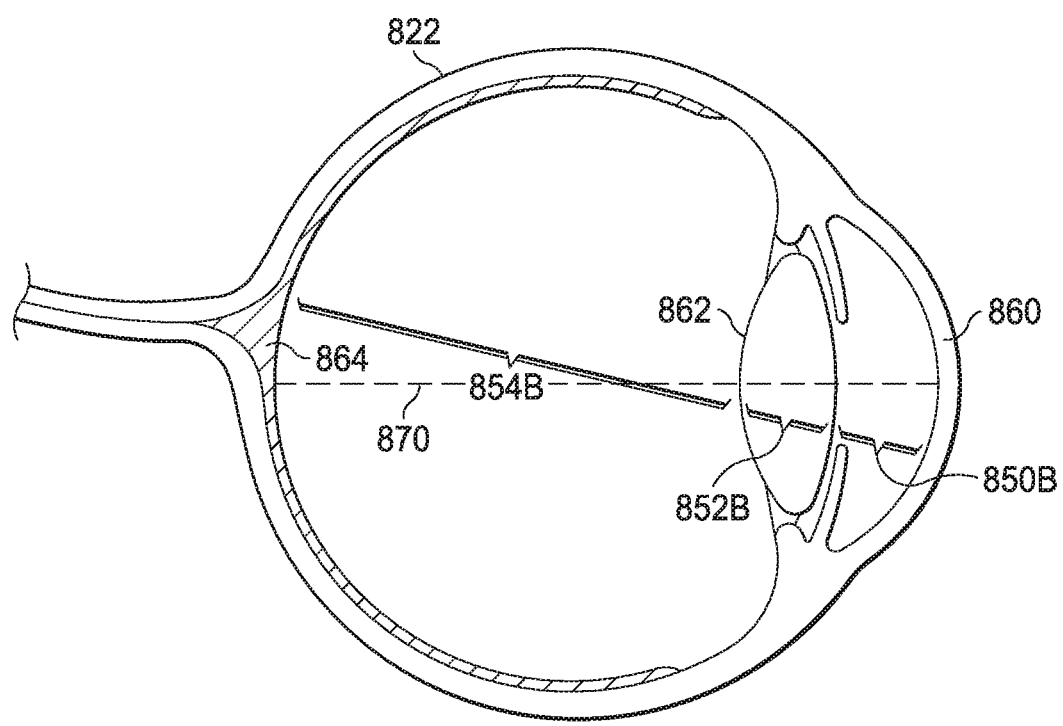

In a fourth example, the at least one distance measurement of the eye of the current patient may include a distance measurement 850B from cornea 860 of eye 822 to lens 862 of eye 822, as illustrated in FIG. 8H. In a fifth example, the at least one distance measurement of the eye of the current patient may include a distance measurement 852B of lens 862, as illustrated in FIG. 8H. In a sixth example, the at least one distance measurement of the eye of the current patient may include a distance measurement 854B from lens 862 of eye 822 to retina 864 of eye 822, as illustrated in FIG. 8H. Measurements 850B, 852B, and 854B may be off axis measurements. Measurements 850B, 852B, and 854B may be off an axis 870.

Figure 8I:
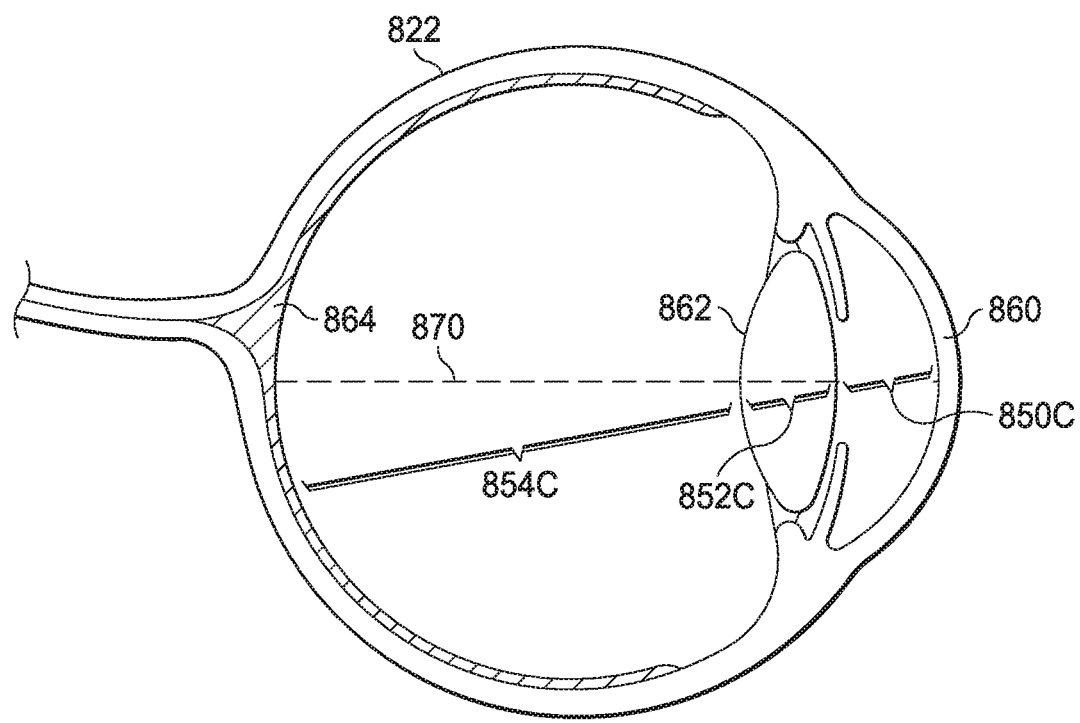

In a seventh example, the at least one distance measurement of the eye of the current patient may include a distance measurement 850C from cornea 860 of eye 822 to lens 862 of eye 822, as illustrated in FIG. 8I. In an eighth example, the at least one distance measurement of the eye of the current patient may include a distance measurement 852C of lens 862, as illustrated in FIG. 8I. In a ninth example, the at least one distance measurement of the eye of the current patient may include a distance measurement 854C from lens 862 of eye 822 to retina 864 of eye 822, as illustrated in FIG. 8I. Measurements 850C, 852C, and 854C may be off axis measurements. Measurements 850C, 852C, and 854C may be off axis 870.

Figure 8J:
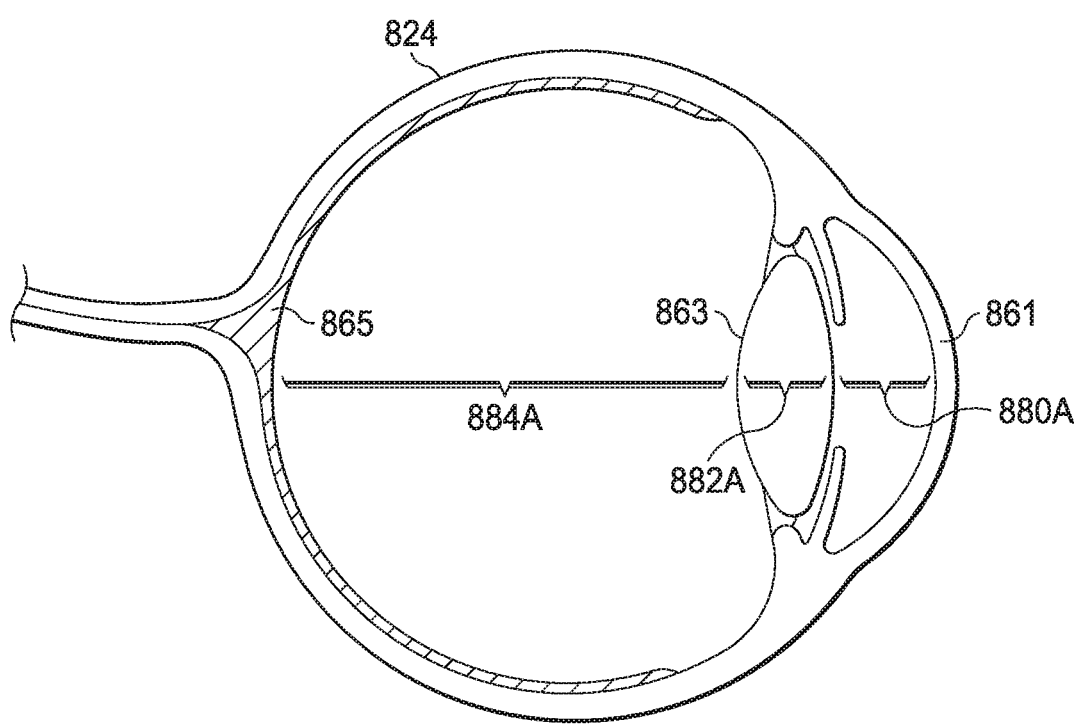
FIGS. 8J-8L illustrate examples of measurements of another eye of a current patient.

In a tenth example, the at least one distance measurement of the eye of the current patient may include a distance measurement 880A from a cornea 861 of eye 824 to a lens 863 of eye 824, as illustrated in FIG. 8J. In an eleventh example, the at least one distance measurement of the eye of the current patient may include a distance measurement 882A of lens 863, as illustrated in FIG. 8J. In a twelfth example, the at least one distance measurement of the eye of the current patient may include a distance measurement 884A from lens 863 of eye 824 to a retina 865 of eye 824, as illustrated in FIG. 8J. Measurements 880A, 882A, and 884A may be on axis measurements.

Figure 8K:
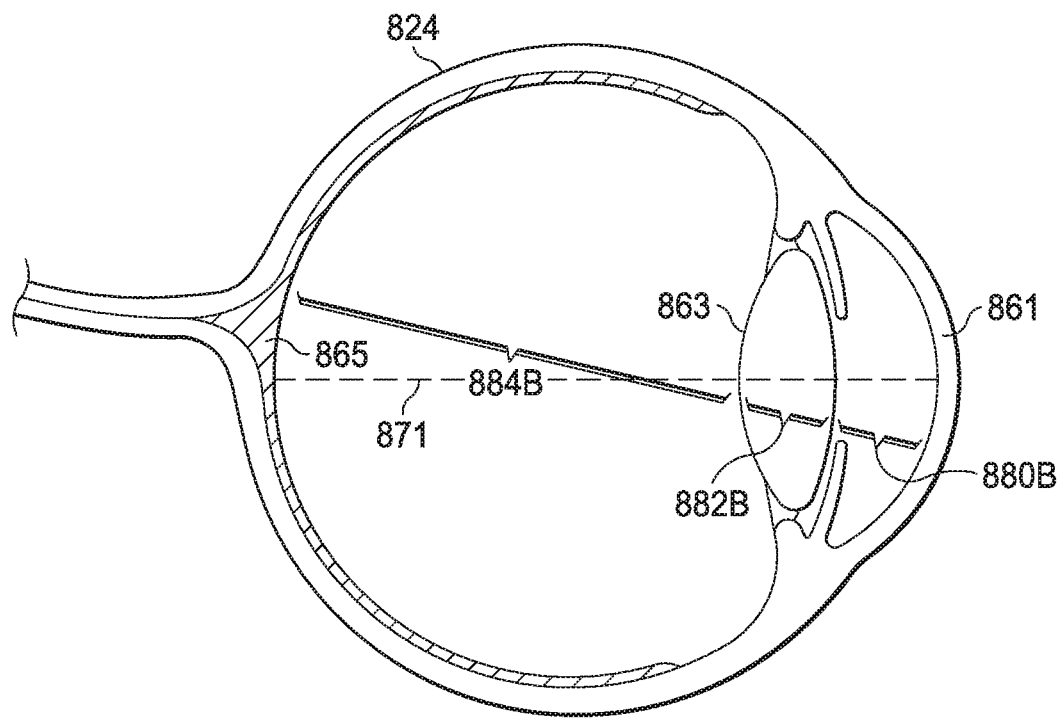

In a thirteenth example, the at least one distance measurement of the eye of the current patient may include a distance measurement 880B from cornea 861 of eye 824 to lens 863 of eye 824, as illustrated in FIG. 8K. In a fourteenth example, the at least one distance measurement of the eye of the current patient may include a distance measurement 882B of lens 863, as illustrated in FIG. 8K. In a fifteenth example, the at least one distance measurement of the eye of the current patient may include a distance measurement 884B from lens 863 of eye 824 to retina 865 of eye 824, as illustrated in FIG. 8K. Measurements 880B, 882B, and 884B may be off axis measurements. Measurements 880B, 882B, and 884B may be off an axis 871.

Figure 8L:
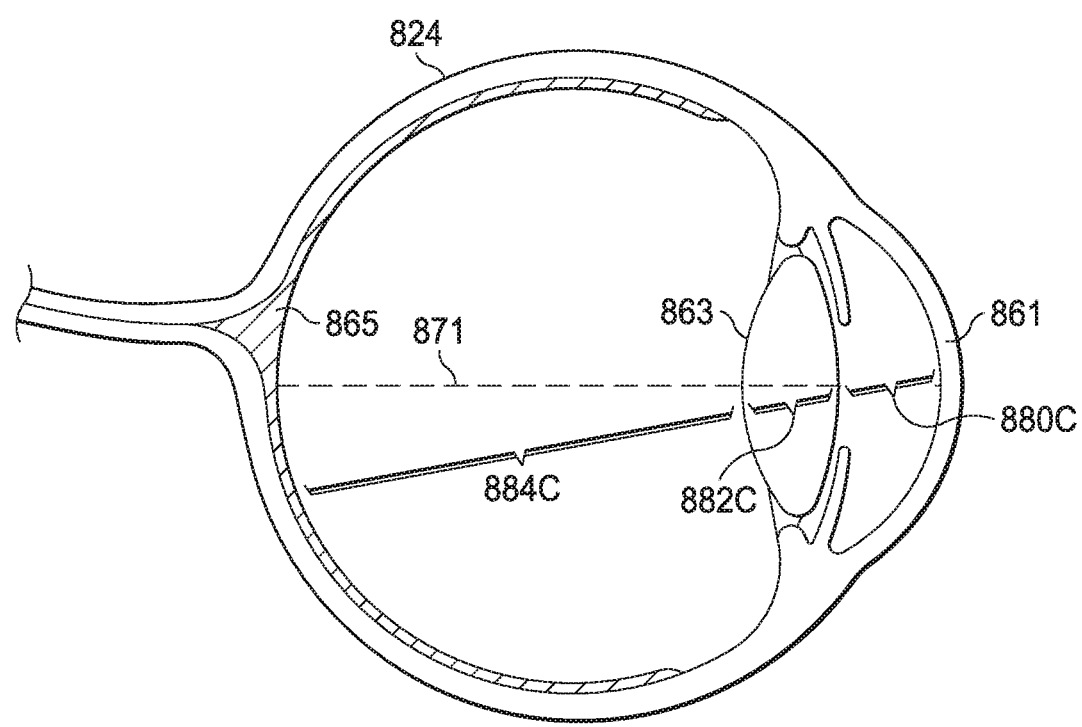

In a sixteenth example, the at least one distance measurement of the eye of the current patient may include a distance measurement 880C from cornea 861 of eye 824 to lens 863 of eye 824, as illustrated in FIG. 8L. In a seventeenth example, the at least one distance measurement of the eye of the current patient may include a distance measurement 882C of lens 863, as illustrated in FIG. 8L. In an eighteenth example, the at least one distance measurement of the eye of the current patient may include a distance measurement 884C from lens 863 of eye 824 to retina 865 of eye 824, as illustrated in FIG. 8L. Measurements 880C, 882C, and 884C may be off axis measurements. Measurements 880C, 882C, and 884C may be off axis 871.

At 730, an angle between a first iris structure of the second multiple iris structures and a second iris structure of the second multiple iris structures may be determined. Determining an angle between a first iris structure of the second multiple iris structures and a second iris structure of the second multiple iris structures may include determining an angle between a first iris structure of the second multiple iris structures and a second iris structure of the second multiple iris structures with respect to a center of a pupil of the eye of the current patient.

In one example, determining an angle between a first iris structure of the second multiple iris structures and a second iris structure of the second multiple iris structures with respect to a center of a pupil of the eye of the current patient may include an angle $\theta_3$ between iris structures 834A and 834B of eye 822, as illustrated in FIG. 8C. In a second example, determining an angle between a first iris structure of the second multiple iris structures and a second iris structure of the second multiple iris structures with respect to a center of a pupil of the eye of the current patient may include an angle $\theta_4$ between iris structures 834A and 834C of eye 822, as illustrated in FIG. 8D. In a third example, determining an angle between a first iris structure of the second multiple iris structures and a second iris structure of the second multiple iris structures with respect to a center of a pupil of the eye of the current patient may include an angle $\theta_5$ between iris structures 836A and 836B of eye 824, as illustrated in FIG. 8E. In another example, determining an angle between a first iris structure of the second multiple iris structures and a second iris structure of the second multiple iris structures with respect to a center of a pupil of the eye of the current patient may include an angle $\theta_6$ between iris structures 836A and 836C of eye 824, as illustrated in FIG. 8F.

At 735, a distance between the first iris structure of the second multiple iris structures and the center of the pupil of the eye of the current patient may be determined. In one example, a distance 810 between iris structure 834A and a center of a pupil of eye 822 may be determined. In another example, a distance 840 between iris structure 836A and a center of a pupil of eye 824 may be determined.

At 740, a distance between the second iris structure of the second multiple iris structures and the center of the pupil of the eye of the current patient may be determined. In one example, a distance 812 between iris structure 834B and the center of a pupil of eye 822 may be determined. In another example, a distance 842 between iris structure 836B and the center of a pupil of eye 824 may be determined.

At 745, a distance between a third iris structure of the second multiple iris structures and the center of the pupil of the eye of the current patient may be determined. In one example, a distance 814 between iris structure 834C and the center of the pupil of eye 822 may be determined. In another example, a distance 844 between iris structure 836C and the center of a pupil of eye 824 may be determined.

At 750, it may be determined if the second multiple iris structures match the first multiple iris structures. If the second multiple iris structures do not match the first multiple iris structures, an indication that the first eye has not been correctly identified may be provided, at 755. In one example, providing an indication that the first eye has not been correctly identified may include providing one or more of icon 420C and text 430C, among others. In another example, providing an indication that the first eye has not been correctly identified may include providing one or more audible sounds. Providing the one or more audible sounds may include providing one or more audible alert and/or warning sounds.

If the second multiple iris structures match the first multiple iris structures, it may be determined if the at least one distance measurement of the eye of the current patient matches the at least one distance measurement associated with the first eye, at 760. In one example, determining if at least one distance measurement of the eye of the current patient matches at least one distance measurement associated with the first eye may include determining if a distance of distances 850-854 matches a respective distance of distances 210-214. In another example, determining if at least one distance measurement of the eye of the current patient matches at least one distance measurement associated with the first eye may include determining if a distance of distances 880-884 matches a respective distance of distances 210-214.

If the at least one distance measurement of the eye of the current patient does not match the at least one distance measurement associated with the first eye, the method may proceed to 755. If the at least one distance measurement of the eye of the current patient matches the at least one distance measurement associated with the first eye, an indication that the first eye has been correctly identified may be provided. For example, one or more of icon 420D and text 430D, among others, may be provided.

At 770, medical procedure information may be retrieved based at least on one of the identification of the first patient and the second multiple iris structures of the eye of the current patient. For example, system 300 may retrieve medical procedure information from a database. System 300 may retrieve the medical procedure information from a database based at least on one of the identification of the first patient and the second multiple iris structures of the eye of the current patient. In one example, the database may key multiple medical procedure information by identifications of patients. In another example, the database may key multiple medical procedure information by iris structures of respective eyes of respective patients.

At 775, the medical procedure information may be provided via at least one of a display and a microscope integrated display. For example, the medical procedure information may include steps of a medical procedure. The steps of the medical procedure may include an ordered series of steps of the medical procedure.

One or more of the method and/or process elements and/or one or more portions of a method and/or processor elements may be performed in varying orders, may be repeated, or may be omitted. Furthermore, additional, supplementary, and/or duplicated method and/or process elements may be implemented, instantiated, and/or performed as desired. Moreover, one or more of system elements may be omitted and/or additional system elements may be added as desired.

A memory medium may be and/or may include an article of manufacture. For example, the article of manufacture may include and/or may be a software product and/or a program product. The memory medium may be coded and/or encoded with processor-executable instructions in accordance with one or more flowcharts, systems, methods, and/or processes described herein to produce the article of manufacture.

The above disclosed subject matter is to be considered illustrative, and not restrictive, and the appended claims are intended to cover all such modifications, enhancements, and other implementations which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A medical system, comprising:
   at least one processor; and
   a memory medium that is coupled to the at least one processor and that includes instructions, when executed by the at least one processor, cause the medical system to:
   receive an identification of a first patient;
   retrieve, based at least on the identification of the first patient, first eye identification information that includes a first plurality of iris structures associated with a first eye of the first patient, a first iris structure of the first plurality of iris structures is separated from a second iris structure of the first plurality of iris structures by a first angle with respect to a center of a pupil of the first eye;
   determine a second plurality of iris structures of an eye of a current patient, a first iris structure of the second plurality of iris structures is separated from a second iris structure of the second plurality of iris structures by a second angle with respect to a center of a pupil of the eye of the current patient;
determine if the second plurality of iris structures match the first plurality of iris structures by determining if second angle matches the first angle;
if the second plurality of iris structures match the first plurality of iris structures, provide an indication that the first eye has been correctly identified; and
if the second plurality of iris structures do not match the first plurality of iris structures, provide an indication that the first eye has not been correctly identified.

2. The medical system of claim 1, wherein:
the first eye identification information further includes at least one distance measurement associated with the first eye; and
the instructions further cause the medial system to:
determine at least one distance measurement of the eye of the current patient;
determine if the at least one distance measurement of the eye of the current patient matches the at least one distance measurement associated with the first eye;
if the second plurality of iris structures match the first plurality of iris structures and the at least one distance measurement of the eye of the current patient matches the at least one distance measurement associated with the first eye, perform providing the indication that the first eye has been correctly identified; and
if the at least one distance measurement of the eye of the current patient does not match the at least one distance measurement associated with the first eye, perform providing the indication that the first eye has not been correctly identified.

3. The medical system of claim 2, wherein:
the at least one distance measurement associated with the first eye includes at least one of a distance measurement from a cornea of the first eye to a lens of the first eye, a distance measurement from a lens of the first eye to a retina of the first eye, a corneal thickness of the first eye, and a lens thickness of the first eye; and
the at least one distance measurement associated with the eye of the current patient includes at least one of a distance measurement from a cornea of the eye of the current patient to a lens of the eye of the current patient, a distance measurement from a lens of the eye of the current patient to a retina of the eye of the current patient, a corneal thickness of the eye of the current patient, and a lens thickness of the eye of the current patient.

4. The medical system of claim 1, wherein the instructions further cause the medical system to:
retrieve medical procedure information based at least on one of the identification of the first patient and the second plurality of iris structures of the eye of the current patient.

5. The medical system of claim 4, wherein the instructions further cause the medical system to:
provide, via at least one of a display and a microscope integrated display, the medical procedure information.

6. The medical system of claim 1, wherein:
the first iris structure of the first plurality of iris structures is at a first distance from the center of the pupil of the first eye;
the first iris structure of the second plurality of iris structures is at a second distance from the center of the pupil of the eye of the current patient; and to determine if the second plurality of iris structures match the first plurality of iris structures, the instructions further cause the medical system to determine if the second distance matches the first distance.

7. The medical system of claim 1, wherein:
the current patient is the first patient; and
the eye of the current patient is a second eye of the first patient, different from the first eye.

8. A method of operating a medical system, comprising:
receiving an identification of a first patient;
retrieving, based at least on the identification of the first patient, first eye identification information that includes a first plurality of iris structures associated with a first eye of the first patient, a first iris structure of the first plurality of iris structures is separated from a second iris structure of the first plurality of iris structures by a first angle with respect to a center of a pupil of the first eye;
determining a second plurality of iris structures of an eye of a current patient, a first iris structure of the second plurality of iris structures is separated from a second iris structure of the second plurality of iris structures by a second angle with respect to a center of a pupil of the eye of the current patient;
determining if the second plurality of iris structures match the first plurality of iris structures by determining if second angle matches the first angle;
if the second plurality of iris structures match the first plurality of iris structures, providing an indication that the first eye has been correctly identified; and
if the second plurality of iris structures do not match the first plurality of iris structures, providing an indication that the first eye has not been correctly identified.

9. The method of claim 8, wherein the first eye identification information further includes at least one distance measurement associated with the first eye;
the method further comprising:
determining at least one distance measurement of the eye of the current patient;
determining if the at least one distance measurement of the eye of the current patient matches the at least one distance measurement associated with the first eye;
if the second plurality of iris structures match the first plurality of iris structures and the at least one distance measurement of the eye of the current patient matches the at least one distance measurement associated with the first eye, performing the providing the indication that the first eye has been correctly identified; and
if the at least one distance measurement of the eye of the current patient does not match the at least one distance measurement associated with the first eye, performing the providing the indication that the first eye has not been correctly identified.

10. The method of claim 9, wherein:
the at least one distance measurement associated with the first eye includes at least one of a distance measurement from a cornea of the first eye to a lens of the first eye, a distance measurement from a lens of the first eye to a retina of the first eye, a corneal thickness of the first eye, and a lens thickness of the first eye; and
the at least one distance measurement associated with the eye of the current patient includes at least one of a distance measurement from a cornea of the eye of the current patient to a lens of the eye of the current patient, a distance measurement from a lens of the eye of the current patient to a retina of the eye of the current patient, a corneal thickness of the eye of the current patient, and a lens thickness of the eye of the current patient.

11. The method of claim 8, further comprising:
retrieving medical procedure information based at least on one of the identification of the first patient and the second plurality of iris structures of the eye of the current patient.

12. The method of claim 11, further comprising:
providing, via at least one of a display and a microscope integrated display, the medical procedure information.

13. The method of claim 8, wherein:
the first iris structure of the first plurality of iris structures is at a first distance from the center of the pupil of the first eye;
the first iris structure of the second plurality of iris structures is at a second distance from the center of the pupil of the eye of the current patient; and
the determining if the second plurality of iris structures match the first plurality of iris structures includes determining if the second distance matches the first distance.

14. The method of claim 8, wherein:
the current patient is the first patient; and
the eye of the current patient is a second eye of the first patient, different from the first eye.

* * * * *